(12) United States Patent
Jiang

(10) Patent No.: US 7,718,131 B2
(45) Date of Patent: May 18, 2010

(54) METHODS AND APPARATUS FOR IMAGING AND PROCESSING OF SAMPLES IN BIOLOGICAL SAMPLE CONTAINERS

(75) Inventor: Yonggang Jiang, New Milton (GB)

(73) Assignee: Genetix Limited, Hampshire (GB)

( * ) Notice: Subject to any disclaimer, the term of this patent is extended or adjusted under 35 U.S.C. 154(b) by 1350 days.

(21) Appl. No.: 11/174,733

(22) Filed: Jul. 6, 2005

(65) Prior Publication Data

US 2007/0009395 A1    Jan. 11, 2007

(51) Int. Cl.
*G01N 21/64*    (2006.01)

(52) U.S. Cl. .................. 422/82.08; 422/82.05; 356/319; 356/326; 382/133; 436/165; 436/172

(58) Field of Classification Search ................ 356/319, 356/326; 382/133; 422/82.05, 82.08; 436/165, 436/172
See application file for complete search history.

(56) References Cited

U.S. PATENT DOCUMENTS

| | | | |
|---|---|---|---|
| 4,580,895 A * | 4/1986 | Patel | 356/39 |
| 5,243,041 A * | 9/1993 | Fernandez-Pol | 536/23.5 |
| 5,499,097 A | 3/1996 | Ortyn et al. | |
| 5,589,351 A | 12/1996 | Harootunian | |
| 6,130,745 A | 10/2000 | Manian et al. | |
| 6,388,788 B1 * | 5/2002 | Harris et al. | 359/196.1 |
| 6,400,487 B1 | 6/2002 | Harris et al. | |
| 6,441,894 B1 | 8/2002 | Manian et al. | |
| 2002/0090320 A1 | 7/2002 | Burow et al. | |
| 2003/0032039 A1 | 2/2003 | Cunningham et al. | |
| 2006/0290926 A1 * | 12/2006 | Masters et al. | 356/319 |

FOREIGN PATENT DOCUMENTS

| | | |
|---|---|---|
| EP | 1 293 783 A2 | 3/2003 |
| EP | 1 358 936 A2 | 11/2003 |
| EP | 1 358 937 A1 | 11/2003 |
| WO | WO 97/10055 | 3/1997 |
| WO | WO 00/66269 | 11/2000 |
| WO | WO 01/96880 A1 | 12/2001 |
| WO | WO 2004/074820 A2 | 9/2004 |

* cited by examiner

*Primary Examiner*—Jill Warden
*Assistant Examiner*—Paul S Hyun
(74) *Attorney, Agent, or Firm*—Foley & Lardner LLP

(57) ABSTRACT

Disclosed herein is a holder for biological sample containers such as well plates. The holder comprises a flat vacuum bed surrounded by a seal. A container is placed within the seal and a vacuum is applied, pressing and flattening the lower surface of the sample container against the flat vacuum bed. Samples in all portions of the container may then be imaged without the need to refocus on each portion of the container. For imaging, a sample in a well can be illuminated by a beam of light arranged so that a part or all of the sample is illuminated by direct rays that have not passed through the well plate. The beam is redirected to other parts of the well if a single illumination does not cover the whole well, so that the sample to be imaged using a series of partial images.

27 Claims, 8 Drawing Sheets

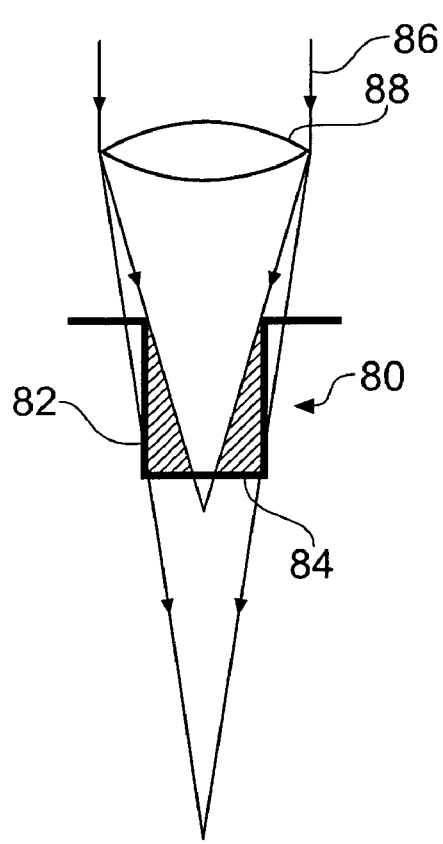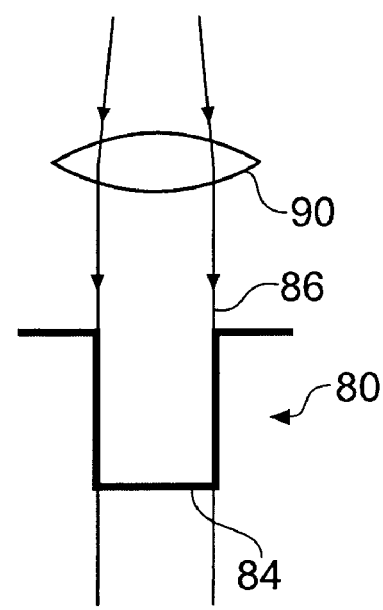
Fig. 8A
Fig. 7
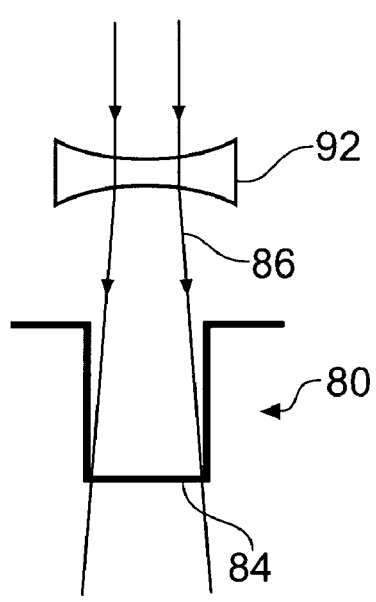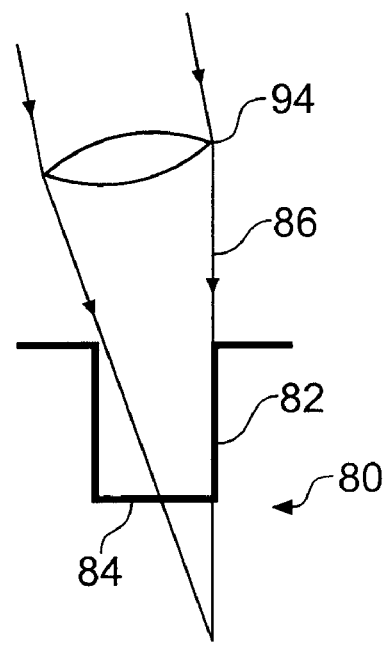
Fig. 8B
Fig. 8C

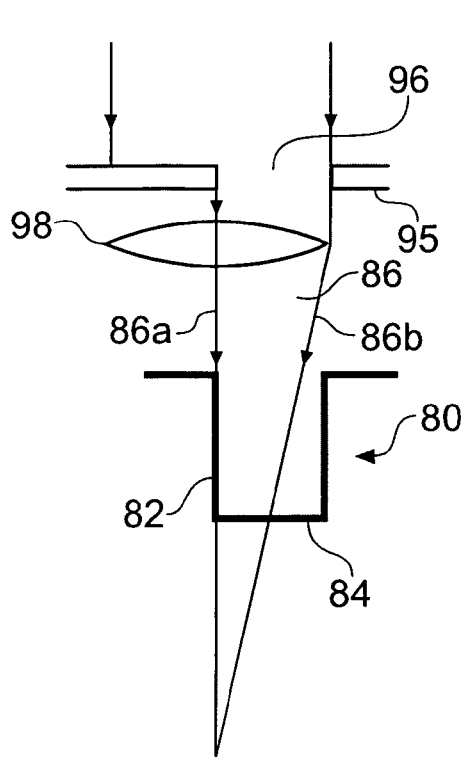
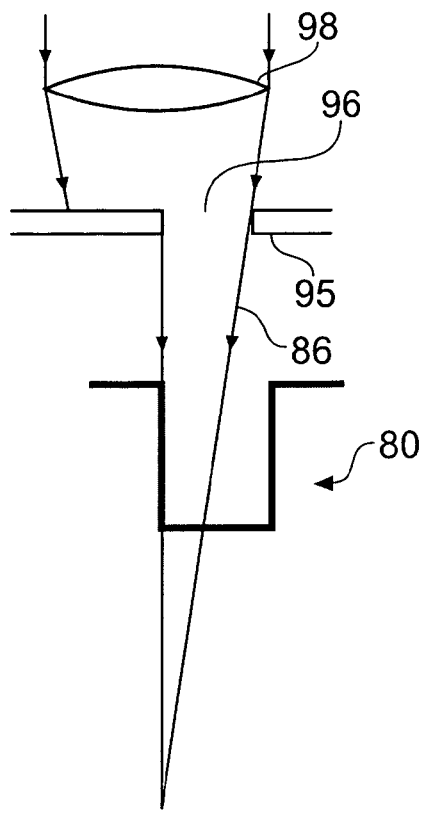
Fig. 9A          Fig. 9B
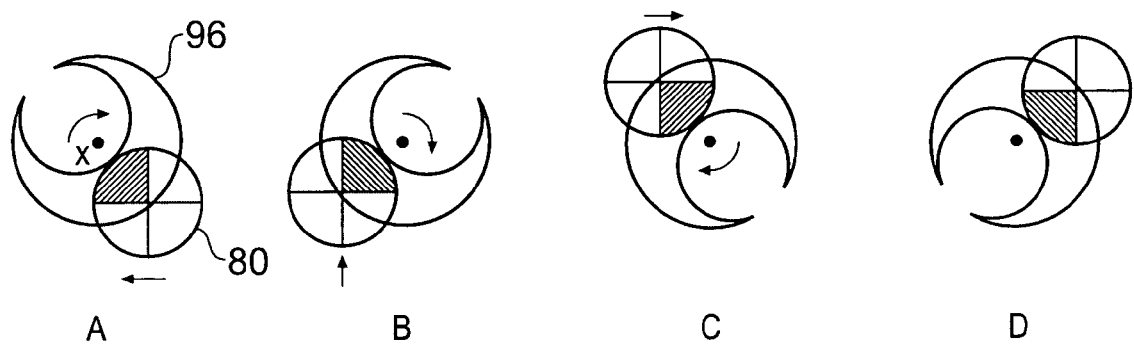
Fig. 10

METHODS AND APPARATUS FOR IMAGING AND PROCESSING OF SAMPLES IN BIOLOGICAL SAMPLE CONTAINERS

BACKGROUND OF THE INVENTION

The present invention relates to methods and apparatus for processing samples in biological sample containers such as well plates, such as imaging of the samples.

Biological samples such as animal cells are commonly cultured in containers such as well plates, omni trays, Q-trays and Petri dishes. Much of the processing of the samples can be performed automatically using robotic apparatus that can deliver containers to and from various stations at which the samples can be observed and imaged using camera equipment, and transferred to other containers using an array of pins on a movable mechanical head.

For successful imaging, it is necessary to be able to accurately position the sample in the field of view of an imaging camera, and to focus the camera on the cells of interest. Also, for general imaging, the cells need to be evenly illuminated for a good quality image, whereas in the case of observations such as fluorescence imaging, one needs to be able to focus the beam of light used to excite the fluorescence onto the relevant cells. For focusing applications, autofocus systems are preferable owing to the automated nature of the robotic apparatus.

U.S. Pat. No. 6,130,745 [1] and U.S. Pat. No. 6,441,894 [2] describe a technique for focussing a beam of laser light used to excite fluorescence in cells cultured in wells in a well plate. It is important to accurately position a tightly focussed beam within the cell colony so as to avoid exciting fluorescence in unbound fluorescent markers outside the colony. The method involves focussing the laser beam near the lower surface of the base of a well, and detecting light reflected back. The focal point is scanned upwards along the vertical axis of the well. The reflected light reaches a maximum when the light is focussed on the surface because scattering of the light is reduced at this point. Thus, the lower surface of the well base is detected. The thickness of the base (as given by the well plate manufacturer) is then added to this position so that the focussed spot can be moved to a point just inside the well, above the base, where the cell colony is located. Accuracy of the technique depends on the quality of the well plate; unknown variations in the base thickness from well to well will affect how the spot is positioned with respect to the upper surface of the base in each well. An alternative arrangement to avoid this issue which involves moving the focussed spot down onto the upper surface of the well base is more difficult to implement. The reflected signal is weaker owing to the refractive index change at the surface boundary being reduced by the fluid in the well.

With regard to focusing a camera to image the cells, a standard autofocus system may be adequate. However, for a container requiring many images, such as a well plate comprising 96, 384 or 1536 wells, it is very time-consuming to refocus the camera for each well. This is particularly problematic if no stains or fluorescent tags are used to highlight the cells; the visual contrast between the cells and their surroundings can be insufficient for the optical feedback in the autofocus system to function efficiently. As an example, under these conditions it can take over an hour to image each well in a 96-well plate by refocusing the camera for every well. A laser range finder system could be used to locate the required focal point for each well, but this is also relatively slow, and very costly.

Other problems associated with imaging samples in containers such as well plates include difficulties in illuminating the samples for non-fluorescence imaging, where any shadows cast across the samples are undesirable, and the time and complexity involved in imaging a container containing many samples (such as a well plate with many wells) where each sample must be accurately aligned with the imaging equipment.

SUMMARY OF THE INVENTION

Accordingly, a first aspect of the present invention is directed to a holder for holding a biological sample container in a biological sample processing apparatus, the holder comprising: a vacuum bed having a planar surface for receiving a lower surface of a biological sample container; a perimeter portion comprising a seal surrounding the vacuum bed, the seal being dimensioned to receive a lower perimeter edge of a biological sample container; and an exhaust outlet for evacuating a volume defined by the vacuum bed, the perimeter portion and a biological sample container received on the seal so that the lower surface of the biological sample container is flattened against the planar surface of the vacuum bed.

A holder according to the first aspect is capable of flattening a container of biological samples so that the samples lie in a common plane that is sufficiently flat and well-defined to be considered as a common focal plane for imaging of the samples. Thus, many or all of the samples in a container can be imaged sequentially without the need to refocus an imaging camera for every sample. Instead, the camera can be focused just once on one sample in one region of the container, and the focus retained for imaging the remainder of the container. This significantly speeds up the time needed for handling each container.

The enhanced flatness is also advantageous for cell picking operations in which delicate pins could be damaged by collision with the base of the container. The risk of collision is reduced if any warp in the container is reduced or removed by holding the container against the vacuum bed. The cells being picked may be individual cells or cells of colonies.

Using reduced air pressure or a vacuum to hold containers for processing is also generally advantageous in that the holder can be of simple construction, with no moving parts subject to wear or malfunction. Initial alignment of the container with the holder may be less precise than required for some mechanical holding devices, so that automation of processing and handling of samples in the containers can be simplified. The vacuum holds the container using an even pressure over the base of the container to improve the shape of the container, in contrast with mechanical clamps and the like that may impose pressure at particular points, thus warping and twisting the container.

The holder is generally applicable to biological sample containers, such as omni-trays, Q-trays and Petri dishes. However, it is particularly advantageous where the biological sample container is a well plate, which can hold a great number of samples all of which need to be processed, preferably in an automated manner.

The planar surface can be made with the desired degree of flatness, for example a flatness that varies by less than 50 µm, or a flatness that flattens the lower surface biological sample container so that it varies by less than 50 µm. The flatness needed is a flatness that is less than, preferably much less than, the depth of field required for providing sufficient quality (i.e. sharp focus) images of cells or other biological material in the biological sample container. Typically, this will be easily achieved by a standard glass plate. However, if very high flatness is needed, then the vacuum bed can be made from an optical flat or other forms of precision flat surface.

In some embodiments, at least a portion of the vacuum bed is transparent, to allow imaging of samples in the biological sample container from below. For example, the vacuum bed may be fabricated from glass. Imaging from below is beneficial in that in an automated apparatus for handling containers, the imaging camera can be arranged well away from other components such as a cell picking head which may otherwise obscure the imaging.

The exhaust outlet may be located in the perimeter portion. This is useful in conjunction with a transparent vacuum bed, where the exhaust outlet should be positioned away from the field of view needed for imaging.

The holder may further comprise a mount portion, wherein the vacuum bed and the perimeter portion are adjustably mounted in the mount portion, the mount portion being operable to allow the position of the vacuum bed and the perimeter portion to be adjusted relative to the mount portion. By attaching the mount portion to an apparatus, this allows the flat plane of the lower surface of the container to be adjusted relative to features of the apparatus, such as ensuring that the plane is perpendicular to the optical axis of a camera or parallel to the plane of the tips of an array of pins. To this end, the mount portion may comprise a gimbal system for adjusting the relative position of the vacuum bed and the perimeter portion. Also, the mount portion may be adapted to be fixedly mounted to a portion of a biological sample processing apparatus.

A second aspect of the present invention is directed to a biological sample processing apparatus comprising: a main bed; a holder mounted on the main bed for holding a biological sample container, the holder comprising: a vacuum bed having a planar surface for receiving a lower surface of a biological sample container; a perimeter portion comprising a seal surrounding the vacuum bed, the seal being dimensioned to receive a lower perimeter edge of a biological sample container; and an exhaust outlet for evacuating a volume defined by the vacuum bed, the perimeter portion and a biological sample container received on the seal so that the lower surface of the biological sample container is flattened against the planar surface of the vacuum bed; and a pump connectable to the exhaust outlet and operable to remove air from the said volume.

The apparatus may further comprise an imaging camera operable to image samples in a biological sample container held by the holder. The holder may be adjustably mounted on the main bed to allow the position of a biological sample container held by the holder to be adjusted relative to the imaging camera. At least a portion of the vacuum bed may be transparent, with the imaging camera arranged under the main bed and operable to image samples in a biological sample container held by the holder through the vacuum bed. The apparatus may be operable to provide relative movement between the imaging camera and a biological sample container held by the holder so that samples in different regions of the biological sample container can be imaged. The imaging camera may comprise an autofocus facility operable to focus the imaging camera on a sample in a biological sample container held by the holder.

The apparatus may further comprise a controller operable to: relatively position the imaging camera and a biological sample container held by the holder so that the imaging camera is in a position for imaging one region of the biological sample container; operate the autofocus facility to determine a focal length to focus the imaging camera on a sample in the one region; lock the imaging camera at the focal length determined by the autofocus facility; and repeatedly relatively position the imaging camera and the biological sample container to obtain images of samples in a plurality of regions of the biological sample container. Thus, automated imaging of all or many samples in a container is made possible without the need to refocus the camera for every sample. This gives much more rapid processing of each container, particularly in the case where feedback for the autofocus system is hampered by lack of contrast from a stain or fluorescent tag, leading to slow focusing.

Alternatively, the apparatus may further comprise a controller operable to: for each of a subset of regions of a biological sample container held by the holder, relatively position the imaging camera and the biological sample container so that the imaging camera is in a position for imaging the region and operate the autofocus facility to determine a focal length to focus the imaging camera on a sample in the region; calculate an average focal length from the determined focal lengths; lock the imaging camera at the average focal length; and repeatedly relatively position the imaging camera and the biological sample container to obtain images of samples in a plurality of regions of the biological sample container, where the plurality is larger than the subset. This takes slightly longer than relying on a single focusing operation for the entire container, but may give more accurate focusing and hence better images if there is any doubt that the increased flatness of the container is not sufficient for single focusing to be relied upon. In the case where the biological sample container is a well plate, each well of the well plate comprises a region of the biological sample container, and the subset of regions of the biological sample container may comprise each of a plurality of wells of the well plate, such as three or four corner wells.

A third aspect of the present invention is directed to a method of holding a biological sample container to facilitate processing of samples in the biological sample container using a biological sample processing apparatus, the method comprising: providing a vacuum bed having a planar surface for receiving a lower surface of a biological sample container; positioning a biological sample container such that its lower surface is adjacent to the vacuum bed; and reducing pressure between the vacuum bed and the biological sample container to flatten the lower surface of the biological sample container against the planar surface of the vacuum bed.

In some embodiments, the method may comprise reducing the air pressure between the vacuum bed and the biological sample container until the flatness of the lower surface of the biological sample container is increased such that the flatness varies by less than 50 μm.

The method may comprise surrounding the vacuum bed with a compressible seal dimensioned to receive a lower perimeter edge of the biological sample container when the container is positioned with its lower surface adjacent to the vacuum bed.

The method may further comprise, after reducing the air pressure: focusing an imaging camera to determine a focal length for imaging a sample in one region of the biological sample container; locking the imaging camera at the focal length determined; and repeatedly relatively positioning the imaging camera and the biological sample container to obtain images of samples in a plurality of regions of the biological sample container.

Alternatively, the method may further comprise, after reducing the air pressure: focusing an imaging camera to determine focal lengths for imaging samples in a subset of regions of the biological sample container; calculating an average focal length from the determined focal lengths; locking the imaging camera at the average focal length; and repeatedly relatively positioning the imaging camera and the biological sample container to obtain images of samples in a plurality of regions of the biological sample container, where the plurality is larger than the subset. For example, the biological sample container may be a well plate, so that each well of the well plate comprises a region of the biological sample container, and the subset of regions of the biological sample container comprises each of a plurality of wells of the well plate, such as three or four corner wells.

At least a portion of the vacuum plate may be transparent, so that the imaging camera can be positioned below the biological sample container and the images obtained through the vacuum bed.

A fourth aspect of the present invention is directed to a method of imaging a biological sample in a well of a well plate, the well defined by a side wall and a base, the method comprising: illuminating the base of the well by directing onto the base of the well a beam of light so that at least part of the base is illuminated by light rays in the beam incident on the base that have not first passed through a part of the well plate, and in the event that only part of the base is so illuminated, repositioning the well and/or the beam to direct the beam onto a further part of the base as many times as necessary for every part of the base to be so illuminated; and recording an image of the biological sample the or each time the base is illuminated.

This method addresses the problems associated with illumination schemes that cast shadows across the sample being imaged. Shadows give a poor quality image which may result in errors when the image is analyzed. According to the invention, a beam of light used to illuminate a sample for imaging is either configured to illuminate the whole sample with direct illumination in a single illumination, or to illuminate only a part of the sample with direct illumination, in which case the beam is then redirected to other parts so that the whole sample can be imaged using a series of images of different parts of the sample. In the former case, the beam of light is directed onto the base so that no light ray in the beam incident on the base passes first through a part of the well plate. Alternatively, the beam of light may be directed onto the base so that at least some light rays in the beam are incident on the base at an oblique angle, and the or each image recorded in a dark field configuration where light from the beam, if not scattered, does not contribute to the image. This is an advantage technique in that an image with good contrast, suitable for image processing, can be obtained without the need for contrast dyes or fluorescent tags.

The oblique angle at which the optical source illuminates the object position is preferably between 10 to 50 degrees, or 20 to 40 degrees, or 25 to 35 degrees to the horizontal. The angle refers to the vertical in the illustrated embodiment, or more generally the optical axis of the collection optics.

In the latter case, the beam of light has a propagation axis and may comprise light rays converging to a focus on the propagation axis so that the beam is defined, in a plane parallel to the propagation axis, by a first light ray parallel to the propagation axis and a second light ray at an angle to the propagation axis; so that the directing may comprise positioning the well in the beam before the focus so that the first light ray is substantially parallel to the side wall of the well. This is a convenient way of achieving partial illumination of the base of the well plate, in the event that complete direct illumination cannot be achieved or is in some way undesirable. In this embodiment, the beam of light may be formed by creating a beam of light with a propagation axis, and arranging in the beam a converging lens centered on the propagation axis and an aperture offset from the propagation axis that passes a fraction of the beam. For example, the converging lens and the aperture may be positioned and the aperture may be shaped and dimensioned to pass a fraction of the beam that illuminates approximately one quadrant of the base. Four illuminations and four partial images are then required to image the whole sample in the well. To achieve quadrant imaging, the aperture may be crescent-shaped with the propagation axis located within the curve of the crescent but outside the aperture. The beam may be directed onto the base four times, each time illuminating a different quadrant of the base, and the repositioning the well and/or the beam may comprise repositioning the beam by rotating the aperture about the propagation axis by 90, 180 or 270 degrees, and repositioning the well by linearly moving the well plate to bring the different quadrants into line with the repositioned beam.

The samples may be cells, in particular animal cells. Moreover, the cells could be individual cells, colonies of cells, cell monolayers or other kinds of cell aggregates. The method can be used for picking valuable or interesting cells or colonies of cells from a cell population. The cells may be 1 to 50 in number in the case of individual cells, or much greater in number in the case of colonies.

The method may further comprise repeating the illuminating and the recording for a plurality of wells in the well plate, often all of the wells or a complete subset of the wells, such as those still known to be active in whatever process that is underway. If only part of the sample is illuminated at one time, so that illuminating every part of the base requires two or more parts of the base to be illuminated, the method may further comprise repeating the illuminating and the recording for many or all wells in the well plate.

To image all parts of each well, the method may comprise: illuminating and recording an image for a first part of each well of the many or all wells; illuminating and recording an image for a second part of each well of the many or all wells; and if necessary repeating the illuminating and recording for further parts of each of the many or all wells until every part of each of the many or all wells has been illuminated.

Alternatively, where the well plate comprises an array of wells arranged in rows, the method may comprise: illuminating and recording an image for a first part of each well in a first row; illuminating and recording an image for a second part of each well in the first row; if necessary repeating the illuminating and recording for further parts of each well in the first row until every part of each well in the first row has been illuminated; illuminating and recording an image for a first part of each well in a second row; illuminating and recording an image for a second part of each well in the second row; if necessary repeating the illuminating and recording for further parts of each well in the second row until every part of each well in the second row has been illuminated; and repeating the illuminating and recording for each further row in the well plate.

Alternatively, where the well plate comprises an array of wells arranged in rows, the method may comprise: illuminating and recording an image for a first quadrant of each well in a first row in a consecutive sequence in a first direction along the row; repositioning the well plate and/or the beam to illuminate a second quadrant of each well; illuminating and recording an image for the second quadrant of each well in the first row in a consecutive sequence in a second direction along the row opposite to the first direction; repositioning the well plate and/or the beam to illuminate a third quadrant of each well; illuminating and recording an image for the third quadrant of each well in the first row in a consecutive sequence in the first direction along the row; repositioning the well plate and/or the beam to illuminate a fourth quadrant of each well; illuminating and recording an image for the fourth quadrant of each well in the first row in a consecutive sequence in the second direction; and repeating the illuminating and recording for each further row in the well plate.

A fifth aspect of the present invention is directed to apparatus for imaging a biological sample in a well of a well plate, the well defined by a side wall and a base, the apparatus comprising: a holder operable to hold a well plate comprising the well containing the sample; an optical beam source operable to generate a beam of light and direct the beam of light onto the base of the well when the well plate is held by the holder so that the whole of the base is illuminated by light rays in the beam incident on the base that have not first passed though a part of the well plate; and an imaging camera operable to record an image of biological sample when the base is illuminated. The apparatus may further comprise a controller operable to control the holder, the optical beam source and the imaging camera to: relatively reposition the holder, the optical beam source and the imaging camera for illuminating and imaging of each well in a well plate held by the holder; illuminate each well; and record an image of each well.

A sixth aspect of the present invention is directed to apparatus for imaging a biological sample in a well of a well plate, the well defined by a side wall and a base, the apparatus comprising: a holder operable to hold a well plate comprising the well containing the sample; an optical beam source operable to generate a beam of light and direct the beam of light onto the base of the well when the well plate is held by the holder so that a part of the base is illuminated by light rays in the beam incident on the base that have not first passed though a part of the well plate; the apparatus being operable to reposition the well plate held by the holder and/or the beam to direct the beam onto a further part or parts of the base, the part and the further part or parts together comprising the whole of the base; and an imaging camera operable to record an image of the biological sample each time the base is illuminated.

The optical beam source may be operable to: generate the beam of light such that the beam of light has a propagation axis and comprises rays converging to a focus on the propagation axis, the focus positioned beyond the well, and the beam being defined, in a plane parallel to the propagation axis, by a first light ray parallel to the propagation axis and a second light ray at an angle to the propagation axis; and to direct the beam such that the first light ray is substantially parallel to the side wall of the well. The optical beam source may comprise a converging lens centered on the propagation axis and an aperture offset from the propagation axis that passes a fraction of the beam. The converging lens and the aperture may be positioned and the aperture may be shaped and dimensioned to pass a fraction of the beam that illuminates approximately one quadrant of the base. The aperture may be crescent-shaped with the propagation axis located within the curve of the crescent but outside the aperture. The apparatus may be operable to reposition the well plate held by the holder and/or the base by rotating the aperture about the propagation axis by 90, 180 or 270 degrees to reposition the beam and by moving the holder holding the well plate to bring a different quadrant into line with the repositioned beam.

The apparatus may further comprise a controller operable to control the holder, the optical beam source and the imaging camera to: relatively reposition the holder, the optical beam source and the imaging camera for illuminating and imaging each of the part and the further part or parts of the base of each well in a well plate held by the holder; illuminate each of the part and the further part or parts; and record an image of each of the part and the further part or parts.

The controller may be further operable to control the holder, the optical beam source and the imaging camera to: illuminate and record an image for a first part of each well; illuminate and record an image for a second part of each well; and if necessary repeat the illuminating and recording for further parts of each well until every part of each well has been illuminated and imaged.

Alternatively, where the holder is operable to hold a well plate comprising an array of wells arranged in wells, and the controller may be further operable to control the holder, the optical beam source and the imaging camera to: illuminate and record an image for a first part of each well in a first row; illuminate and record an image for a second part of each well in the first row; if necessary repeat the illuminating and recording for further parts of each well in the first row until every part of each well in the first row has been illuminated and imaged; illuminate and record an image for a first part of each well in a second row; illuminate and record an image for a second part of each well in the second row; if necessary repeat the illuminating and recording for further parts of each well in the second row until every part of each well in the first row has been illuminated and imaged; and repeat the illuminating and recording for each further row in the well plate.

Alternatively, where the holder is operable to hold a well plate comprising an array of wells arranged in rows, and the optical beam source is operable to illuminate a quadrant of the base, the controller may be further operable to control the holder, the optical beam source and the imaging camera to: illuminate and record an image for a first quadrant of each well in a first row in a consecutive sequence in a first direction along the row; reposition the well plate and/or the beam to illuminate a second quadrant of each well; illuminate and record an image for the second quadrant of each well in the first row in a consecutive sequence in a second direction along the row opposite to the first direction; reposition the well plate and/or the beam to illuminate a third quadrant of each well; illuminate and record an image for the third quadrant of each well in the first row in a consecutive sequence in the first direction along the row; reposition the well and/or the beam to illuminate a fourth quadrant of each well; illuminate and record an image for the fourth quadrant of each well in the first row in a consecutive sequence in the second direction; and repeat the illuminating and recording for each further row in the well plate.

A seventh aspect of the present invention is directed to a method of imaging biological samples in wells of a well plate, the method comprising: defining a path across the well plate that includes each well containing a sample to be imaged; moving the well plate with respect to an optical beam source operable to generate a beam of light to illuminate the sample in a well and an imaging camera operable to record an image of the sample in a well when illuminated so as to bring each well in the path in turn into a position where the sample can be illuminated and imaged, the movement being continuous from a start to an end of the path; and operating the optical beam source and the imaging camera to illuminate and image the sample in a well when each well in the path is in the position where it can be illuminated and imaged.

Imaging an entire well plate (or as many wells in a plate as are of interest) with a single continuous scanning motion offers a number of advantages over techniques where the well plate is separately moved and repositioned to image each well. The well plate can be processed more quickly, components used to provide the motion can be simpler since there is no need for accurate alignment of the well plate with the imaging equipment for every well, wear and tear of such components is reduced since the number of stopping and starting movement per well is vastly reduced, and image quality can be improved since motion of the samples within the wells caused by repeated stopping and starting, which can give blurred images, is removed.

The samples may be cells, in particular animal cells. Moreover, the cells could be individual cells, colonies of cells, cell monolayers or other kinds of cell aggregates.

In some embodiments, operating the imaging camera comprises opening a shutter of the imaging camera for a time period $\Delta t_c$ and operating the optical beam source comprises generating the beam of light for a time period $\Delta t_l$, where $\Delta t_c > \Delta t_l$ and $\Delta t_l$ lies within $\Delta t_c$. Thus the exposure for recording each image is defined by the duration for which the beam is turned on. Many optical sources, such as flash lamps or pulsed laser sources, can be operated swiftly enough for an exposure short enough to avoid a blurred image as the well plate moves past the camera. Using the illumination period to control the brief exposure reduces the requirements on the speed of operation of the camera shutter. 52. The shutter time interval $\Delta t_c$ is preferably at least 2 or 3 orders of magnitude greater than the illumination time interval $\Delta t_l$, perhaps up to 3 or 4 orders of magnitude. Typical values for the time interval $\Delta t_c$ would be in the order of milliseconds or tens of milliseconds, whereas typical values for the time interval $\Delta t_l$ would be from tens of microseconds to a microsecond or lower. For example, $\Delta t_c$ may be around 10 milliseconds and $\Delta t_l$ may be a few microseconds.

If the movement of the well plate has a substantially constant speed, the optical beam source and the imaging camera may be operated at a substantially constant and equal repetition rate. This arrangement provides for recording of images at the appropriate time without the need for synchronization of the well plate movement with the beam source and camera operation beyond initial starting of the movement and illumination and imaging cycles at the appropriate times.

In the event that the optical beam source and the imaging camera are operable to illuminate and image only a part of each well in each operation of the optical beam source and the imaging camera and are further operable to illuminate a further part or parts of the well in further operations, the method may comprise: defining a path across the well plate that includes each part of each well containing a sample to be imaged; moving the well plate so as to bring each part in the path in turn into a position where the sample can be illuminated and imaged; and operating the optical beam source and the imaging camera to illuminate and image the sample in a well when each part is in the position where it can be illuminated and imaged.

The well plate is preferably arranged in a vacuum holder comprising a bed with a planar surface so that a lower surface of the well plate is flattened by vacuum pressure against the planar surface of the vacuum bed, thereby to ensure that the wells of the well plate are co-planar. With the wells being held at the same height in this way, the scan path can be traversed with a fixed focus of the imaging camera when recording the images from the wells along the path. The need to refocus on each well is therefore eliminated. Furthermore it becomes possible to obtain slice images at a variety of depths in the well. This can be accomplished by traversing the path with each of a plurality of fixed focuses of the imaging camera focused at different depths down the wells, so that multiple sets of images from the wells along each path are recorded corresponding to multiple well depths.

An eighth aspect of the present invention is directed to apparatus for imaging biological samples in wells of a well plate, the apparatus comprising: an optical beam source operable to generate a beam of light for illuminating a sample in a well of a well plate; an imaging camera operable to record an image of the sample when illuminated; and a holder for holding a well plate comprising wells containing samples to be imaged, the holder being operable to move the well plate with respect to the optical beam source and the imaging camera to bring each well in a path defined across the well plate that includes each well containing a sample to be imaged in turn into a position where the sample can be illuminated and imaged, the movement being continuous from a start to an end of the path; the optical beam source and the imaging camera being further operable to illuminate and image the sample in a well when each well in the path is in the position where it can be illuminated and imaged. The imaging camera may be operable by opening a shutter of the imaging camera for a time period $\Delta t_c$, and optical beam source may be operable to generate the beam of light for a time period $\Delta t_l$, where $\Delta t_c > \Delta t_l$ and $\Delta t_l$ lies within $\Delta t_c$. For example, $\Delta t_c$ may be substantially 10 ms and $\Delta t_l$ may be substantially 3 μs. Also, the holder may be operable to move the well plate at a substantially constant speed and the optical beam source and the imaging camera may be operable to illuminate and image at a substantially constant and equal repetition rate.

The holder may comprise: a vacuum bed having a planar surface for receiving a lower surface of a well plate; a perimeter portion comprising a seal surrounding the vacuum bed, the seal being dimensioned to receive a lower perimeter edge of a well plate; and an exhaust outlet for evacuating a volume defined by the vacuum bed, the perimeter portion and a well plate received on the seal so that the lower surface of the well plate is flattened against the planar surface of the vacuum bed.

Optionally, the imaging camera comprises a focus facility, which may be autofocus or manual focus, operable to focus the imaging camera on a sample in a well of a well plate held by the holder.

The apparatus may comprise a controller operable to: relatively position the imaging camera and a well plate held by the holder so that the imaging camera is in a position for imaging one well of the well plate; operate the focus facility to determine a focal length to focus the imaging camera on a sample in the one well; and lock the imaging camera at the focal length determined by the focus facility during imaging of samples along the path of movement. Refocusing for each well is not necessary, since planarity is ensured by the vacuum holder.

In an alternative mode of operation, the controller may be operable to: relatively position the imaging camera and a well plate held by the holder so that the imaging camera is in a position for imaging one well of the well plate; operate the focus facility to determine multiple focal lengths to focus the imaging camera in the one well; and lock the imaging camera at each of the multiple focal lengths determined by the focus facility while imaging samples along the path of movement, so that the path is traversed repeatedly at each focal length and multiple sets of images from the wells along each path are recorded corresponding to multiple well depths. A sequence of image "slices" at different well depths can thus be recorded. The different focal planes may be determined from a single focusing activity, with the other focal planes taken at fixed offsets from the single focus, or may be determined from multiple independent focusing activities.

In some embodiments, the optical beam source and the imaging camera may be operable to illuminate and image only a part of each well in each operation of the optical beam source, and further operable to illuminate a further part or parts of the well in further operations; the holder may be operable to move the well plate to bring each part of each well in a path defined across the well plate that includes each part of each well containing a sample to be imaged in turn into the position where the sample can be illuminated and imaged; and the optical beam source and the imaging camera may be further operable to illuminate and image the sample in a well when each part in the path is in the position where it can be illuminated and imaged.

BRIEF DESCRIPTION OF THE DRAWINGS

For a better understanding of the invention and to show how the same may be carried into effect reference is now made by way of example to the accompanying drawings in which:

FIG. 7 shows a schematic side view of an arrangement for illuminating a sample in a well of a well plate with a beam of light, for imaging of the sample with a camera;

FIGS. 8A, 8B and 8C show schematic side views of arrangements for illuminating a sample in a well of a well plate with a beam of light according to embodiments of the invention;

FIGS. 9A and 9B show schematic side views of arrangements for illuminating a sample in a well of a well plate with a beam of light according to further embodiments of the invention;

FIG. 10 shows a series of schematic plan views illustrating steps in a method for illuminating a sample in a well of a well plate using the embodiments of FIGS. 9A and 9B;

DETAILED DESCRIPTION

Figure 1:
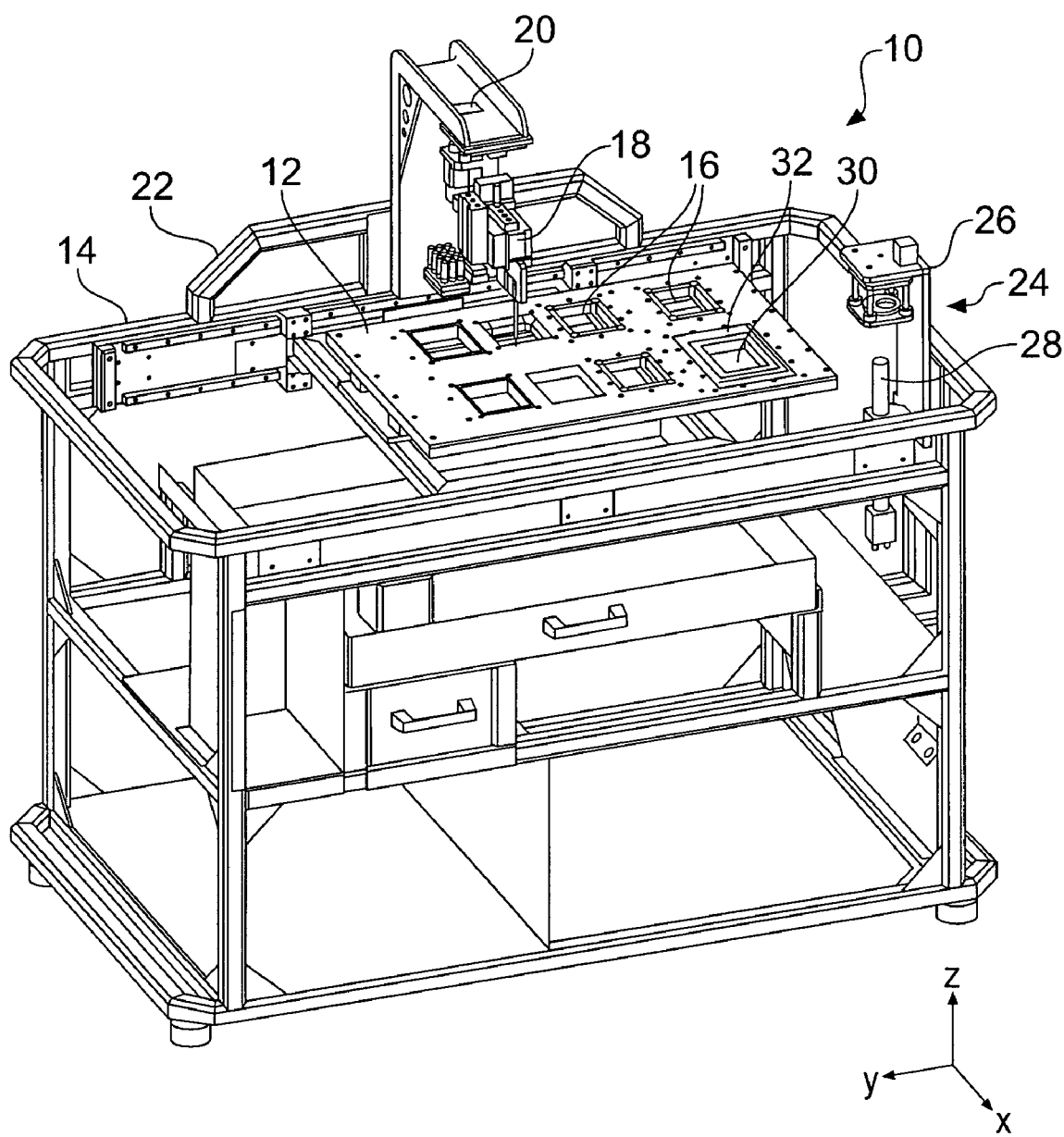
FIG. 1 shows a perspective view of an apparatus for handling and processing biological samples in containers that embodies aspects of the present invention.

FIG. 1 is a perspective view of an apparatus for handling and processing biological samples that embodies aspects of the present invention. However, it is to be understood that the various aspects of the invention may be used with alternative apparatus, containing fewer or more features for handling and processing samples and/or for handling samples in alternative biological sample containers. An example of an alternative apparatus which could be readily adapted to incorporate one or more aspects of the invention is given in EP 1,293,783 [3], the contents of which are incorporated herein by reference.

The apparatus 10 may be understood as a robot for cell picking having an integrated imaging camera. The apparatus can be subdivided notionally into two-half spaces, one above and one below a main bed 12 which is supported by a frame 14. The main bed 12 is mounted on linear positioners (not shown) so as to be movable relative to the frame 14 in the x and y directions, under the control of a controller (not shown). The controller may be a computer connected by electronic links using standard interface protocols to various automated components of the apparatus 10, with control of the apparatus effected by control software resident in the computer.

A cell picking head 18 is provided that comprises a plurality of hollow pins for aspirating animal cells, allowing cells to be picked from one container and deposited in another container. The cell picking head 18 is suspended over the main bed 12 from a gantry 20 by way of a head positioning system made up of x-, y- and z-linear positioners operable to move the cell picking head 18 over the main bed 12. The gantry 20 is mounted on a rail 22 attached to the frame 14 and can slide therealong to give further movement of the cell picking head 18 relative to the main bed 12. All movements can be controlled by the controller.

The main bed 12 contains a plurality of stations 16 (in this case eight) being apertures adapted to receive biological sample containers (not shown) and possibly also components such as a wash/dry station for cleaning the pins after picking. In this example, the apertures are rectangular and shaped to received biological sample containers in the form of well plates, such as plates containing 96 wells. However, other containers such as omni trays, Q-trays and Petri dishes may also be handled by providing suitable stations, or using adapters that fit into the well plate stations to hold the containers. The x and y movement of the main bed 12 can be used in conjunction with the movement of the cell picking head 18 to accurately position the pins of the head 18 over particular wells in the well plates. Also, the main bed 12 can be moved to the right hand end of the frame 14 (as illustrated) to bring an imaging station 30 to an imaging assembly 24.

The imaging assembly 24 is mounted on the frame 14, and comprises a light beam source 26 positioned in the upper half space to direct light downwards onto a well plate held in the imaging station 30, and an imaging camera 28 positioned in the lower half space and directed upwards to image cells cultured in the well plate when illuminated by the light source 26. The imaging station 30 includes a holder 32 mounted on the main bed 12 for holding a biological sample container, in this case a well plate.

Figure 2:
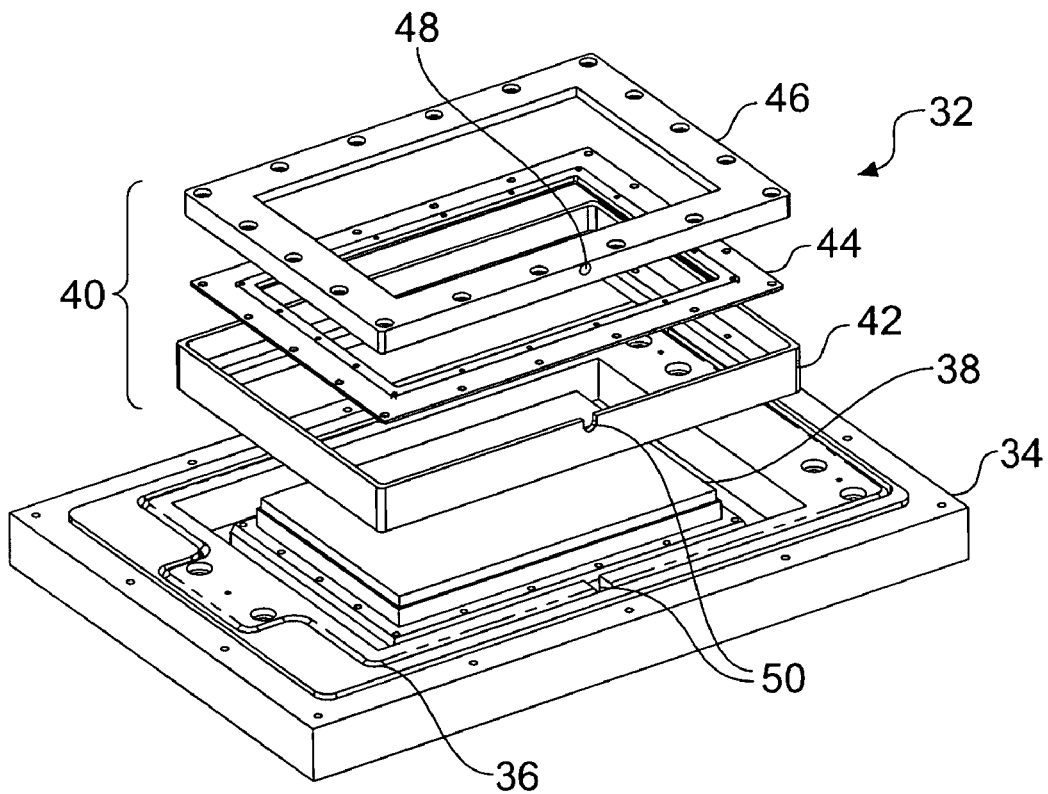
FIG. 2 shows an exploded perspective view of a holder for holding a biological sample container according to an embodiment of the invention.

FIG. 2 shows an exploded perspective view of the holder 32. The holder 32 comprises a mount portion 34 which has the form of a generally rectangular ring defining an aperture and is adapted to be fastened to the main bed 12 in the imaging station 30. The mount portion 34 receives within its aperture a base portion 36 which extends across the aperture. The base portion 36 is movably fixed to the mount portion 34 by way of a gimbal system (not shown) that allows the position of the base portion to be adjusted relative to the mount portion 34 and hence relative to the main bed 12 and other components of the apparatus 10.

A central region of the base portion 36 is occupied by a vacuum bed 38 which has a horizontal surface sized and shaped to accommodate the lower surface of a well plate to be held by the holder 32. Also, the surface of the vacuum bed 38 is flat. The bed may be made of, or have a flatness comparable to that of, an optical flat. In other words, its flatness deviates from a truly flat plane by an amount small enough to be expressed in terms of wavelengths of light. The vacuum bed 38 is made of glass, so that the imaging camera 28 can image through the holder 32 when the holder 32 is held in the imaging station 30 and positioned above the imaging camera 28.

The holder further comprises a perimeter portion 40, which in turn comprises three substantially rectangular ring-shaped portions. An upper clamp portion 46 fits within a lower clamp portion 42, with a flexible compressible vacuum seal 44 sandwiched between the two clamp portions. When assembled, the perimeter portion 40 has the form of a rectangular ring that fits into the base portion 36 and surrounds the vacuum bed 38 so that the seal 44 is disposed around the outer perimeter of the vacuum bed 38. A portion of the seal 44 adjacent the vacuum bed is exposed and is dimensioned to receive the lower outer edge of a well plate.

The upper clamp portion 46 includes a vacuum or exhaust outlet 48 that passes through the thickness of the ring of the upper clamp portion. The lower clamp portion 42 and the base portion 36 have corresponding notches 50 in their edges that allow a line from a vacuum pump to be connected to the exhaust outlet when the various parts of the holder 32 are assembled.

Figure 3:
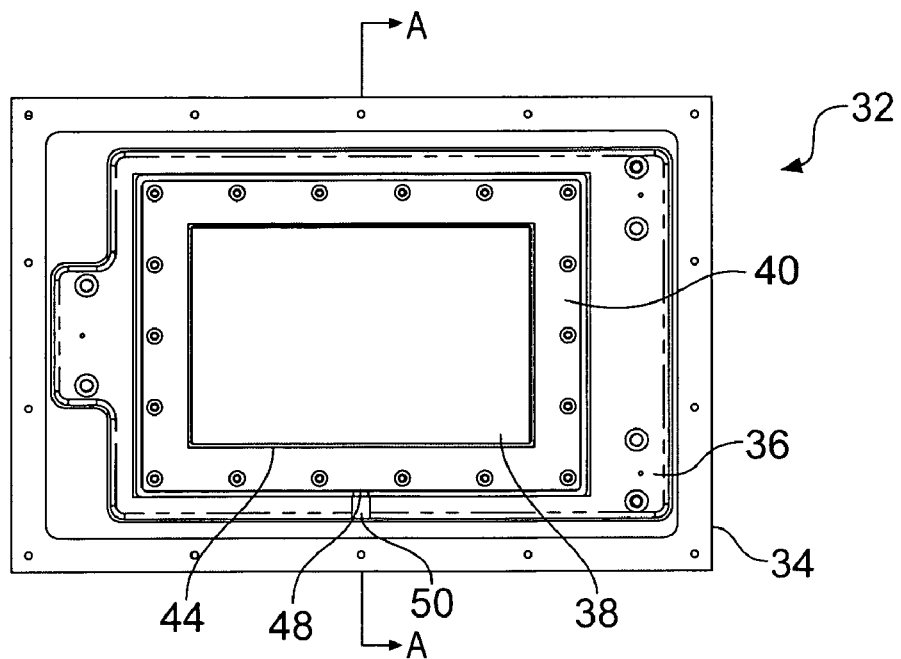
FIG. 3 shows a plan view of the holder of FIG. 2.

FIG. 3 shows a plan view of the assembled holder 32 from above. This shows how the seal 44 surrounds the vacuum bed 38, and illustrates the opening formed by the notches 50 that gives access to the exhaust outlet 48.

Figure 4:
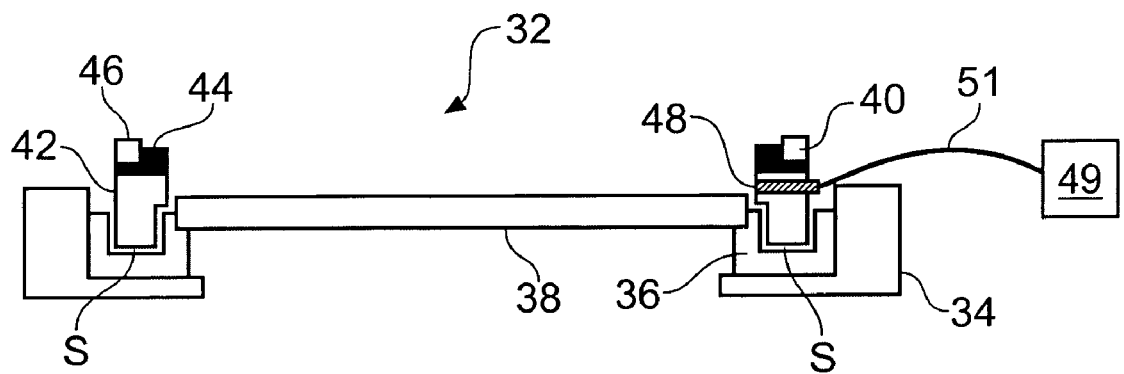
FIG. 4 shows a cross-sectional view of the holder of FIGS. 2 and 3.

FIG. 4 shows a cross-sectional view through the assembled holder 32 along the line A-A in FIG. 3, again showing how the seal 44 surrounds the vacuum bed 38. The exhaust outlet 48 is shown connected to a vacuum pump 49 by a line 51 (not to scale). The purpose of this is explained further below.

Figure 5A:
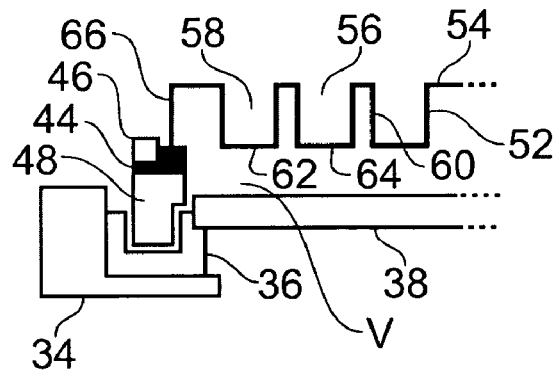
FIGS. 5A and 5B show partial cross-sectional views of the holder of FIGS. 2 and 3 in use.

FIG. 5A shows a partial cross-sectional view through the assembled holder 32, showing a first stage in the use of the holder 32. The holder 32 is to be used to hold a well plate 52. A well plate is a biological sample container made of glass or plastic, preferably clear so that light excitation and/or collection may be performed through it. The well plate 52 has an upper surface 54 having an array of circular apertures 56 which are openings of an array of wells 58, each of which can contain samples of cells. Each well 58 comprises a cylindrical side wall 60 that extends down from the rim of the aperture 56, and a base 62. Together the bases 62 define a lower surface 64 of the well plate 52. In this example, the individual bases are flat. Other well plates have hemispherical or otherwise curved bases, in which case when they are pulled against the planar surface of the vacuum bed 38 they will contact it tangentially, so that the well plate will have multiple tangential points of contact. Also extending down from the upper surface 54, all around the edge of the well plate 52, is a side portion 66, which terminates in a lower perimeter edge or rim substantially at the level of the lower surface 64 of the well plate 52.

Figure 5B:
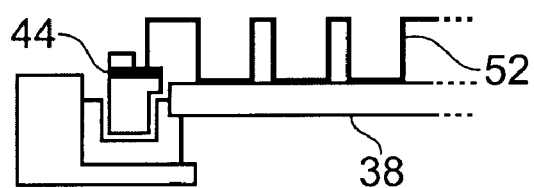

The well plate 52 is placed on the holder 32 such that its lower rim rests on the seal 44, as shown in FIG. 5. Thus positioned, a volume V is defined by the lower surface 64 of the well plate 52, the vacuum bed 38 and the perimeter portion 40. Although FIGS. 4, 5A and 5B show a gap between the perimeter portion 40 and the base portion 36, it is to be understood that these portions in fact closely fit together, perhaps including a seal, so that the gap is air-tight.

FIG. 5B shows a partial cross-sectional view through the assembled holder 32, showing a second stage in the use of the holder 32. Once the well plate 52 is positioned on the seal 44, air is pumped out of the volume V using the vacuum pump 49 connected to the exhaust outlet 48. As the air pressure in the volume V is reduced, the seal 44 is compressed by the rim of the well plate 52 and the lower surface 64 of the well plate 52 is brought into close contact with the vacuum bed 38. Sufficient air is removed so that the well plate 52 is pressed tightly against the vacuum bed 38, so that the lower surface 64 of the well plate 52 conforms to the shape of the vacuum bed 38. In other words, the lower surface 64 substantially or partially acquires the extreme flatness of the vacuum bed 38. The reduced air pressure is maintained while images are obtained of the cells in the well plate 52 using the imaging apparatus 24. Then, when the well plate is to be removed, the air pressure in the volume V is restored via the exhaust outlet 48 so that the rim of the well plate 52 is released from the seal 44.

Improving the flatness of the lower surface of the well plate 52 in this way allows the process of obtaining images of cells in the individual wells to be enhanced. Generally, the lower surface of a well plate or other biological sample container will have a degree of warp, which may typically be such that there is a height variation across the surface of about 600 μm. This variation is necessarily repeated in the relative positions of layers of cells in the different wells. When imaging the cells, a very precise and narrow depth of field less than 600 μm is required, since the cells are very small and the image should not be cluttered and confused by other items being included in the focal plane of the imaging camera. Therefore, without the holder of the present invention, it is generally necessary to refocus the imaging camera for each well. This is time-consuming. In the event that the cells do not contain any contrast agent or fluorescent tags that distinguish the cells from the gel or other medium in which they are cultured, the problem is increased because there may be insufficient contrast for any autofocus system on the imaging camera to accurately focus the camera within a reasonable time, so that the focussing procedure becomes protracted. As an example, it can take about one hour to image every well in a 96 well plate, which is inconveniently slow for an automated system intended to handle many cell samples.

In contrast, the vacuum system of the present invention can improve the flatness of the well plate so that the height variation across the lower surface is less than 50 μm. This is sufficiently flat that all the cells in the various wells across the plate lie within a single focal plane with respect to the imaging camera and the necessary shallow depth of field. Thus, the camera can be focussed just once, on the cells in any one of the wells, and the same focus used to image every well. Usefully, the camera will be equipped with an autofocus system and be under control of the apparatus controller or a separate controller, so the focussing and imaging is wholly automated. Alternatively, a manual or semi-manual focus may be performed and may be preferred in a low cost machine. This becomes a practical option with the invention, since only one focus is required per well plate or other biological sample container. Thus, a method for imaging an entire well plate can comprise the steps of:

1. positioning a well plate containing cells to be imaged on the holder;
2. removing air from the holder to press the base of the well plate against the vacuum bed of the holder to improve the flatness of the well plate;
3. select a single well containing a sample of cells and position it in the field of view of the imaging camera;
4. focus the camera on the cells of interest in the well;
5. lock the focus of the camera at the focal length determined in step 4; and
6. move the camera and/or the holder holding the well plate (maintaining their relative positions in the vertical direction) to bring some or all of the wells of the plate sequentially into the field of the view of the imaging camera to record an image of cells in each well.

Using this technique, all wells in a 96 well plate can be imaged in 5 to 10 minutes, roughly an order of magnitude improvement over not using a vacuum holder to hold the well plate.

The imaging system can be arranged to focus on more than one well of the well plate (or more than one region if the container is not a well plate). A subset of perhaps 3, 4 or up to ten wells can be selected, distributed across the well plate. The necessary focal length required to image cells in each of the wells can be measured, and an average focal length calculated which is then used to image every well in the plate. The controller controlling the camera can be used to perform these functions. For the specific example of the well plate, a useful subset comprises each of the four corner wells, although any selection of two or more wells may be used. This method can be used to eliminate any errors that may result if the plane of the vacuum bed is not perfectly parallel with the plane of motion of the xy-positioners used to scan across the well plate, since the multiple points will define a plane for the xy-positioners to scan in, rather than a single point which will then need the xy-positioners to assume that the vacuum bed plane is parallel to the xy-positioning plane. To make multiple focuses, steps 3-5 of the above method can be revised as follows:

3. select a subset of wells each containing a sample of cells and position each in turn in the field of view of the imaging camera;
4. focus the camera on the cells of interest in each of the wells in the subset and record each focal length;
5. calculate an average focal length from the recorded focal lengths and lock the focus of the camera at the average value.

Although this takes a little longer than focussing on just one well or just one region of a container, it is still vastly quicker and more efficient than refocusing the camera for every image required across a whole container.

Various modifications may be made to the holder 32 as depicted in FIGS. 2-5. For example, the vacuum bed may be modified so that only a portion of it is made from a transparent material such as plastic or glass, if it is not desired to image every part of the biological sample container. Further in this regard, the vacuum bed may be entirely opaque, and can be used with an imaging assembly in which the camera is arranged above the main bed of the apparatus to image the cells directly rather than through the base of the container.

For an opaque or transparent vacuum bed, the holder is also of use in conjunction with a cell picking head for picking operations involving particularly delicate pins coming into close proximity with the base of the container, where the pins could be damaged by collision with the base. The risk of collision is reduced if the base is made more uniformly flat.

It may be convenient to arrange for the exhaust outlet to be positioned in the vacuum bed rather than in the perimeter portion; this is likely to be most relevant in the event that an opaque vacuum bed is used, where the exhaust outlet will not get in the way of imaging upwards through the vacuum bed.

Springs may be provided under the perimeter portion, where this part sits in the base portion (the location marked "S" in FIG. 4). These work in conjunction with the compression of the seal to give movement of the container towards the vacuum bed as the air pressure is reduced, and also work to raise the container upwards and release it from the vacuum bed when the air pressure is increased.

The gimbal system provided in the holder shown in FIG. 2 allows the container, once held on the holder by the reduced air pressure, to be moved and adjusted relative to the imaging assembly, the cell picking head or other equipment provided on the apparatus. For example, the flat plane of the lower surface of the container and the vacuum bed can be adjusted so as to be more exactly perpendicular to the optical axis of the imaging camera to ensure that the flat plane remains parallel to the focal plane of the focussed camera as the camera is moved to image different regions of the container, or to be more precisely parallel with the plane of the tips of the array of pins in the head. However, this might be deemed to be unnecessary. In this case, the holder can be simplified by dispensing with the mount portion, and configuring the base portion to be fixedly attachable directly to the main bed.

Indeed, the holder may be generally simplified by eliminating the need for a separate perimeter portion. Only the seal of the perimeter portion need be retained, and this can be fixed directly to the vacuum bed, perhaps by bonding with a suitable adhesive. If the seal is fixed to the upper surface of the vacuum bed, it must be sufficiently compressible for the lower surface of the container to come into contact with the vacuum bed (which will depend on the relative heights of the lower surface and the lower perimeter edge of the container). Alternatively, the seal can be disposed in a recess in the vacuum bed, so that the perimeter edge of the container can travel below the surface of the vacuum bed and thus bring the lower surface of the container into better contact with the vacuum bed. In either case, the volume V is formed by the seal, the vacuum bed and a container positioned on the seal. Also in either case, it is probably most convenient for the exhaust outlet to be located in the vacuum bed, so that it does not obstruct compression of the seal.

Figure 6A:
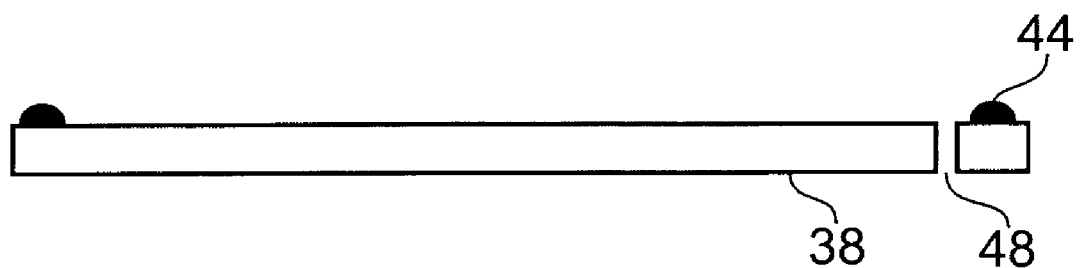
FIGS. 6A and 6B show cross-sectional views of alternative embodiments of a holder for holding a biological sample container according to the invention.
Figure 6B:
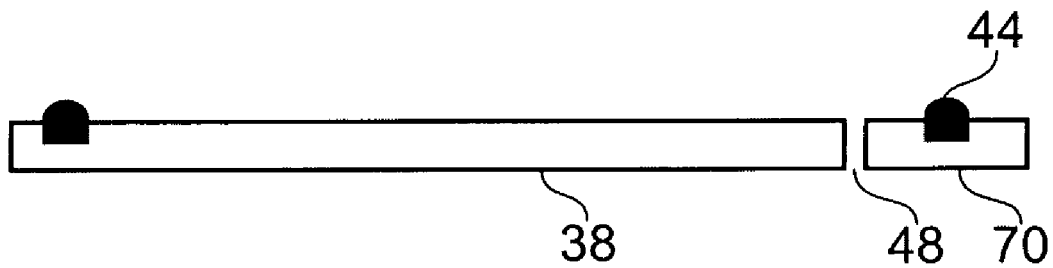

FIGS. 6A and 6B show cross-sectional views of these two alternatives. FIG. 6A shows the seal 44 positioned on the top surface of the vacuum bed 38, and FIG. 6B shows the seal 44 positioned in a ring-shaped recess 70 in the top surface of the vacuum bed. The exhaust outlet 48 passes through the vacuum bed.

For successful imaging of samples in well plates and other containers, it is generally necessary to illuminate the sample with a beam of light from a light source at the same time as recording an image with a camera. The light source may usefully be a light emitting diode (LED), but other sources such as lasers or flash lamps may be used. The choice will depend on factors including the wavelength and the intensity of the light required. To collect as much of the illuminating light as possible with the camera, it is desirable for the beam to be focussed. However, a potential problem with such an arrangement is that the side walls of the container are liable to cast shadows on the sample partially blocking or distorting the passage of light to the base of the wells. This is particularly true in the case of a well in a well plate, where the side walls are relatively high compared with the area of the base, so that much of the base can be in shadow or otherwise obscured.

FIG. 7 is a schematic representation of an illuminated well, showing this problem. A well 80, shown in cross section, has a side wall 82 and a base 84. The well contains a sample of cells to be imaged; the cells are not shown but will be in a layer close to the base, so that illuminating the base is effectively the same as illuminating the sample. An incident light beam 86 is focussed using a converging lens 88, and directed downwardly onto the base 84 so that the base 84 falls wholly within the area of the beam, to illuminate all parts of the base. However, the outer parts of the beam 86 are intercepted by the top surface of the well plate and the side wall 82 of the well 80, so that the outer parts of the base 84 are in shadow (indicated by hatching in the Figure). Only the central part of the base 84 receives direct light. Thus, an image of the whole of the base and hence the whole sample will be partly in darkness or semi-darkness or is imaged in a distorted manner as a result of light partly passing through the well plate.

The present invention seeks to address this by using illumination arrangements that avoid having parts of the illuminating beam passing through parts of the container before reaching the base and the sample. Various embodiments are considered.

FIG. 8A shows a particularly simple arrangement, in which a lens assembly (shown in simplified form as a single converging lens 90) is used to create a collimated light beam 86 of sufficient cross-sectional area to illuminate the whole of the base 84. Further lenses (not shown) may be positioned under the well 80 to collect the light and direct it to a camera for imaging. In this example, the beam is shown as having a width matching that of the well so that no light is wasted, but the beam may have a width greater than that of the well, and still achieve the aim of every part of the base receiving only direct illumination. All of the base is illuminated with a single exposure to the light beam.

FIG. 8B shows an alternative embodiment with which it is also possible to illuminate the whole of the base with one exposure. In this case, a lens assembly 92 with a divergent effect is used to create a diverging beam 86 that is directed down onto the base 84 in such a way that the area of the beam is equal to or greater than the area of the base. Again, collection lenses may be positioned under the well to collect the light for imaging.

FIG. 8C shows an embodiment using a converging light beam 86. As is evident from FIG. 7, it is not possible when using a converging beam for the whole of the base to fall within the beam area without parts of the beam being intercepted by parts of the well plate, so that a shadow is cast on the base. It is therefore proposed that, if using a converging beam (which may be desirable in that no collection lenses are needed under the well plate, for example), only a part of the base is illuminated in one exposure to the light beam, to avoid shadows. According to FIG. 8C, a converging lens assembly 94 is used to generate a standard converging beam 86, that is directed onto the base 84 of the well 80. To ensure illumination up to the edge of the base, the beam is directed at an angle to the plane of the base 84, with the side of the beam substantially parallel to and coincident with the side wall 82.

An image of the sample is taken, and then the well and/or the beam are moved so that a different part of the base is illuminated, when a second image is taken. This is repeated until the whole of the base has been exposed and a set of images that together show the whole sample have been taken. Depending on the intended purpose of the image, image processing techniques can be used to stitch the images together to obtain a composite image showing the whole sample. However, for applications such as cell counting for confluence measurements, this is not necessary.

The arrangement of FIG. 8C may be considered undesirable because of the need to angle the light beam with respect to the base of the well, which then requires a complex relative movement to achieve exposure of the whole base. An alternative approach is shown in FIGS. 9A and 9B.

FIG. 9A shows, similarly to FIG. 8C, a well 80 with a part of its base 84 illuminated with a converging beam arranged to that one side of the beam is parallel to and coincident with the side wall 82 of the well 80. However, in this embodiment the beam comprises only a portion of a standard converging beam 86, selected using mask 95 defining an aperture 96 arranged in the beam path above the well. Correctly positioned with respect to the converging lens 98, the aperture 96 results in a beam 86 which, in cross-section, is defined by a first light ray 86*a* parallel to the propagation direction/propagation axis of the beam 86 and a second light ray 86*b* convergent on the first light ray 86*a*. To achieve this, the aperture 96 is offset from the center of the beam as it is incident on the aperture whereas the lens 98 is centered on the propagation axis; in other words the aperture 96 is asymmetrically positioned with respect to the propagation axis and the lens 98. In this example, the lens 98 is placed after the aperture 96, but a similar effect can be achieved with the lens 98 placed before the aperture 96, as shown in FIG. 9B.

The necessary repositioning of the beam and the well to exposure the various parts of the base are achieved in this embodiment by rotating the mask-defined aperture 96 about the propagation axis of the beam to select different parts of the incoming beam, and using linear motion of the well plate in the x and y directions to align different parts of the well base with the adjusted beam. A range of aperture shapes may be implemented by appropriate shaping of a mask; the resulting beam shape and size will determine how many exposures are required to image the whole sample. For a given beam shape and size, the number of exposures needed will also depend on the size of the well. It has been found that a mask with a crescent-shaped aperture gives a beam shape suitable for illuminating one quadrant of the base. Thus, four exposures are used to image the sample. However, other aperture shapes can be used to illuminate a quadrant of the base.

FIG. 10 shows the sequence of movements required for this imaging. The mask with a crescent-shaped aperture 96 is shown from above superimposed over the well 80, looking down the propagation axis X of the beam. In FIG. 10A, the aperture and well are aligned for exposure of the upper left quadrant of the base, with the side wall of the well closest to the propagation axis where the beam is defined by a ray parallel to the axis and hence parallel to the wall. After an image is taken, the mask in which the aperture is formed is rotated clockwise by 90 degrees and the well is shifted to the left by a distance equal to its width, as indicated by the arrows in FIG. 10A. These movements result in the arrangement of FIG. 10B, in which the upper right quadrant of the base is exposed. After imaging, a further 90 degree clockwise rotation of the mask bearing the aperture and an upward shift of the well (as illustrated; in reality the well is moving in the horizontal plane) give the positions shown in FIG. 10C, in which the lower right quadrant is exposed. After a third image is taken, a third 90 degree clockwise rotation of the mask bearing the aperture and a shift of the well to the right give the positions of FIG. 10D, in which the final, lower left quadrant of the base is exposed and imaged. Thus, every part of the base has been imaged using four exposures, the mask and thus the aperture in it has been rotated about the propagation axis, and the well has described a square about the propagation axis. However, the original incoming beam from the light source has not been adjusted or altered in any way. Depending on the field of view of the camera, it may also be necessary to move the camera to keep the well within the field of view.

Figure 11:
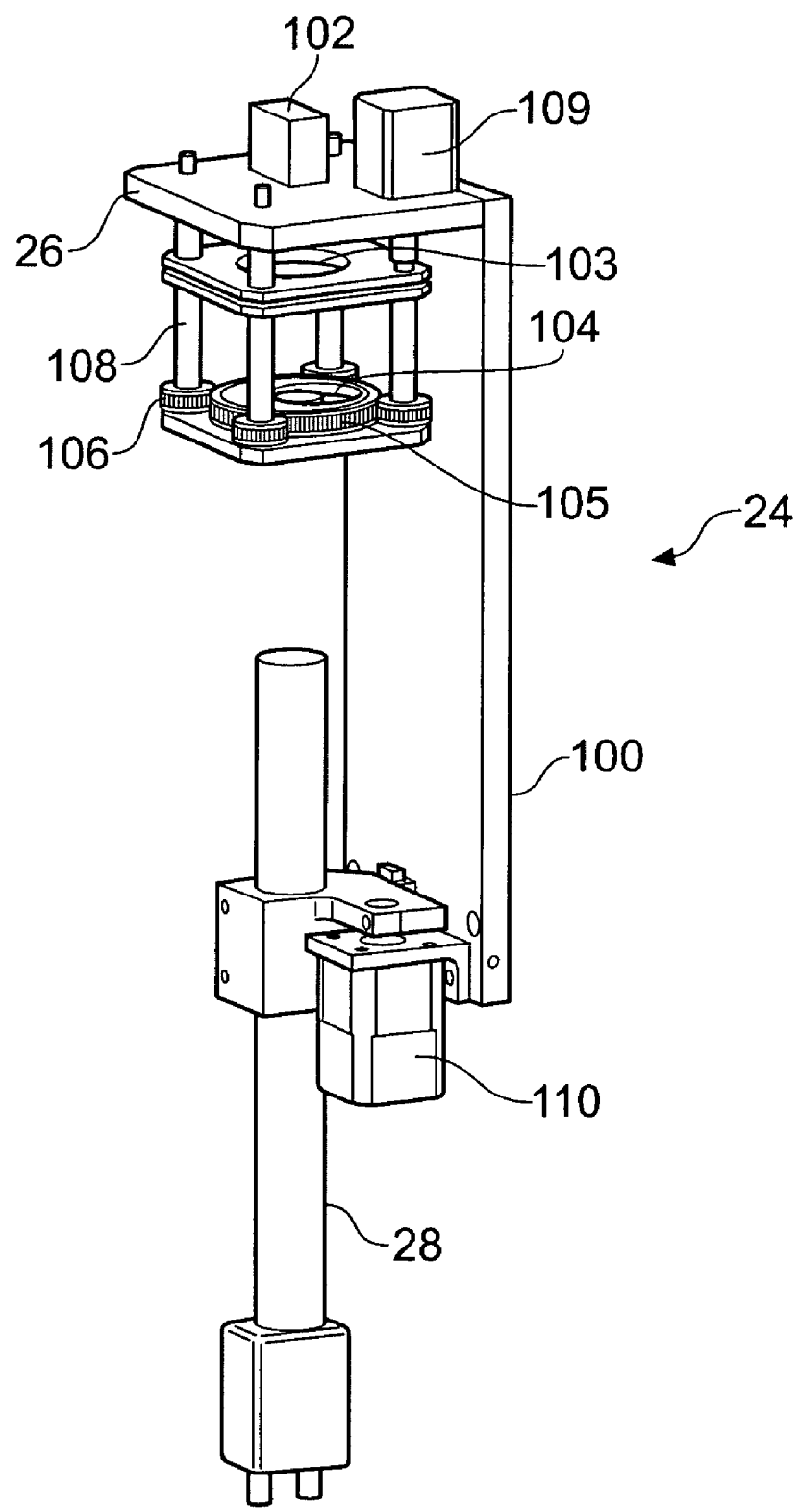
FIG. 11 shows a perspective view of an imaging assembly for recording images of samples in a biological sample container that implements the embodiments of FIGS. 9A and 9B.

FIG. 11 shows a perspective view of apparatus suitable for implementing the imaging technique of FIGS. 9 and 10 using the specific example of quadrant imaging with a mask having a crescent-shaped aperture. An imaging assembly 24, already depicted as part of the apparatus 10 of FIG. 1, comprises a light beam source 26 mounted at the upper end of a bracket 100 and positioned to direct a beam of illuminating light downwards to an imaging camera 28 mounted at the lower end of the bracket 100. The bracket is configured for mounting of the imaging assembly on the frame 14 of the apparatus 10 so that the beam source 26 is above the main bed 12 and the camera 28 is below the main bed 12 (see FIG. 1). In this way, a biological sample in a container held in the imaging station 30 of the main bed 12 can be positioned in the beam path for imaging using the camera. Advantageously, the container is held in a vacuum holder of the type described above, but this is not essential.

The light beam source 26 comprises a housing 102 housing a light source such as an LED. A variety of light sources may be used including LEDs which may be colored or white light emitting, conventional filament light sources, superfluorescent LEDs, diode lasers, other types of solid state laser or gas lasers. Fixed wavelength or tunable diode lasers may be used. The light source emits light downwards through an opening under the housing to provide a beam incident on a converging lens 103 supported under the light source. Suspended below the lens 102 is a flat disk or mask with a rotatable crescent-shaped aperture 104. Rotation is provided by a system of cogs. The mask 105 has a toothed outer edge. Four toothed wheels 106 are rotatably mounted horizontally on vertical axles 108, one at each corner of a square, and positioned so that the teeth of the wheels 106 are engaged with the teeth of the aperture disk 105. A motor 109 mounted on the bracket 100 is connected to at least one of the wheels 106 and is operable to drive the wheel 106 around on its axle 108. The engagement of the teeth of the wheel(s) 106 and the disk 105 causes the disk 105 to rotate in the horizontal plane, thus repositioning the aperture 104 with respect to the converging beam formed by the lens 103.

The camera 28 is directed upwards to image samples in containers held in the light beam by the main bed 12. The camera 28 includes a DC motor 110 operable to control the focus of the camera; with suitable optical feedback this can be used to automatically focus the camera 28 on a sample in a conventional manner (autofocus).

A controller, which may be a combined controller operable to control all features of the apparatus 10, or a dedicated imaging controller, is connected to the imaging assembly 24. The controller will send the necessary instructions to the various parts of the imaging assembly 24 for obtaining images of samples. Namely, a well of a well plate (or a sample-containing region of a different container) is brought into the field of view of the camera and into alignment with the beam source 26, using the x and y movement of the main bed 30. The light source is switched on so that a quadrant of the base of the well is illuminated with a light beam formed by the lens 103 and the aperture 104 of the disk 105, and the camera takes an image of at least the illuminated quadrant, and possibly of the whole well base. The disk and thus the aperture is rotated and the well moved sideways so as to illuminate a second quadrant of the base, and a second image taken, and so on to image all four quadrants. The light source may be switched on separately to provide separate illumination for each image, or may be left on continuously, since the opening of the camera shutter will determine the exposure. In the former case, there is no need to synchronize the illumination with the camera operation. Instead, the camera shutter can be opened for an exposure time that is long compared to a much shorter illumination time, timed to occur during the camera exposure time. Alternatively, the camera shutter can be left open for the duration of the imaging process, and the light source switched on for a brief exposure for each of the aperture/well plate positions. In this case, if the field of view is large enough to include all four quadrants, each of the quadrants can be recorded on the same image.

Although the imaging has been described in terms of moving the well plate, it is to be understood that the required relative movements may also be achieved by keeping the well plate stationary and moving the light source, lenses and aperture mask and the camera instead, or by combining movements of these components with movements of the well plate.

It will be appreciated that this procedure can be readily modified in the event that the beam shaping apparatus provides a beam that illuminates more or less than a single quadrant of the base. Rotation or other movement of the mask bearing the aperture is performed as many times as is necessary to illuminate a total area corresponding to the base, in conjunction with linear horizontal movements of the well plate to align different parts of the base with the reconfigured beam until the whole base has been illuminated.

Embodiments for illuminating the base in sections in which some or all of the light rays within the beam are incident on the base (and hence on a sample of cells in the well) at an oblique angle are of particular relevance to the application of cell confluence detection. It is well known that cell colonies cultured in wells display contact inhibition whereby cell division ceases once the cells have grown across the well to fill the available area and touch each other. The degree to which the cells fill the well is referred to as confluence. If a colony is grown to high or full confluence experiments performed on the cells may be damaged. Thus it is important to determine the confluence. However, the cell growth rate is not generally predictable, and different colonies grow at different rates, so it is standard practice for the confluence to be measured at regular intervals. Measurement may be by direct visual inspection (possibly via a microscope), but this is time-consuming, so the process is preferably automated by taking images of the cells and using image processing to determine the degree of confluence.

It has been found that illuminating the cells from an oblique angle and then recording the image such that the image is taken in a dark field configuration in which light from the illuminating beam, if not scattered, does not contribute to the image, offers enhanced confluence detection. The oblique illumination allows many cell types to be imaged with sufficient contrast for successful imaging processing without the need for fluorescence tagging or staining of the cells. The oblique angle at which the optical source illuminates the object position is preferably between 10 to 50 degrees, or 20 to 40 degrees, or 25 to 35 degrees to the horizontal. The angle refers to the vertical in the illustrated embodiment, or more generally the optical axis of the collection optics.

It will be understood that the cells being imaged could be individual cells, colonies of cells, cell monolayers or other kinds of cell aggregates.

The illumination embodiments of FIGS. 8C, 9A and 9B are relevant to this technique, as are any other arrangements in which the illuminating light beam is arranged to be incident on the cells at an oblique angle, and at the same time not to pass through any part of the well plate before reaching the cells, so that no shadow is cast. For example, the embodiment of FIG. 8C may be modified so that a collimated beam of light is used in place of the convergent beam. Arranging an oblique collimated beam so that at least part of it does not passes through the wall of the well before reaching the cells means that only part of the well base will be illuminated. Hence a plurality of illuminations will be required for imaging of the whole of the base, in accordance with the various possibilities for repositioning of the beam and the well plate as described above.

The preceding description of quadrant imaging has been limited to imaging of a single well. However, in reality, it is more likely that many or all of the wells in a well plate will need to be imaged, as discussed with regard to the vacuum holder. For quadrant imaging, one could proceed by imaging all four quadrants for one well, then moving to the next well and imaging all four quadrants, and so on until each well had been imaged, moving from well to well in a raster scan of the array of wells, for example. However, this requires four rotations of the aperture and four shifts of the well plate for each well, which is a large number of movements for a whole well plate. This is both time-consuming and wearing for the components.

An alternative approach is to scan across the well plate imaging all the upper left quadrants (say), then moving the mask that forms the aperture and shifting the well plate and scanning the well plate to image all the upper right quadrants (say), etc. This reduces the number of times the mask and thus the aperture must be rotated per well plate. However, the total distance traveled by the well plate, and the total number of movements, is still quite large, since the whole plate is scanned four times. Therefore a further alternative is to scan along a single row of wells, imaging a first upper quadrant for each well, then, at the end of the row shift the well plate to allow illumination of the second upper quadrants, and scan back along the same row to image the second upper quadrants. The well plate is thus moved back and forth along the same line, with a small shift along that line in-between. Once back at the start of the row, the well plate is shifted in the orthogonal direction to allow illumination of a first lower quadrant for each well, and then scanned along the whole row for imaging of all of those lower quadrants, shifted at the end of the row along the same direction to give illumination of the second lower quadrants, and scanned back along the row for imaging of the second lower quadrants. The well plate is then shifted in the orthogonal direction again, to line up a first upper quadrant in the adjacent row of wells, and the procedure repeated, until all the wells have been fully imaged. The disk and thus the aperture is rotated at the end of each scan of each row, in combination with the shifts of the well plate.

Figure 12:
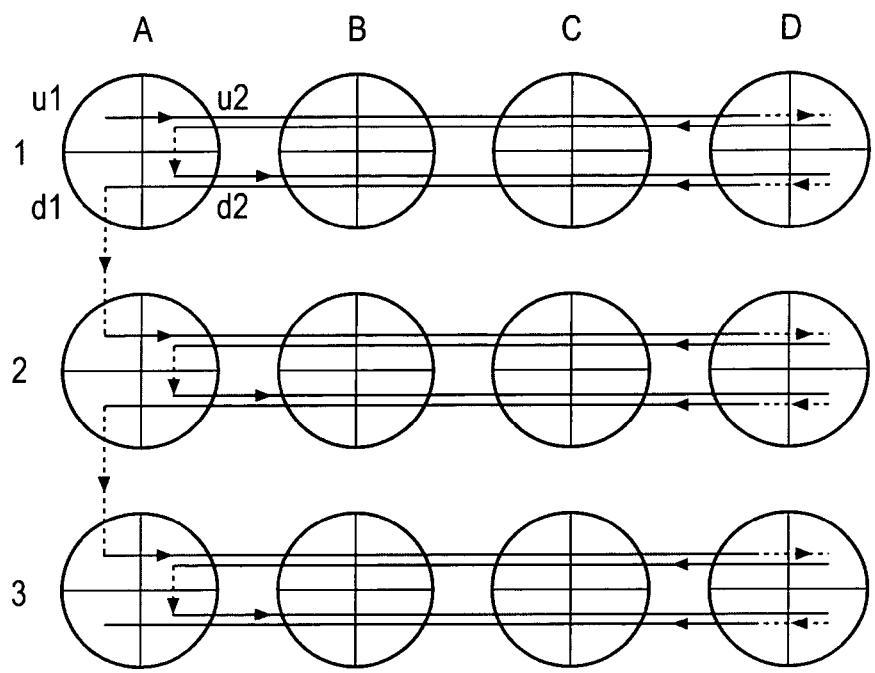
FIG. 12 shows a schematic representation of an array of wells in a well plate and a path to be followed for imaging each well by illuminating and recording an image of each quadrant of each well according to an embodiment of the invention.

FIG. 12 shows a schematic representation of this scanning and imaging regime. A simple array of twelve wells is shown, in rows 1, 2 and 3 and columns A, B, C and D. Each well has four quadrants to be imaged: u1, u2, d1 and d2. The route of the relative movement between the well plate and the illuminating beam necessary to illuminate all the quadrants is shown; the scan follows lines in the direction of the arrows, with the shifts in position of the well plate indicated by the dotted lines. The two horizontal but reverse direction scans for each row of upper and lower quadrants follows the same line, but these are shown slightly vertically separated for clarity. Thus, starting with the upper left quadrant of the upper left well, A1, the quadrants are imaged in the following order, where "(S&R)" indicates a shift of the well plate and a rotation of the aperture:

| A1u1 | B1u1 | C1u1 | D1u1 (S&R) | D1u2 | C1u2 | B1u2 | A1u2 (S&R) |
| A1d2 | B1d2 | C1d2 | D1d2 (S&R) | D1d1 | C1d1 | B1d1 | A1d1 (S&R) |
| A2u1 | B2u1 | C2u1 | D2u1 (S&R) | D2u2 | C2u2 | B2u2 | A2u2 (S&R) |
| A2d2 | B2d2 | C2d2 | D2d2 (S&R) | D2d1 | C2d1 | B2d1 | A2d1 (S&R) |
| A3u1 | B3u1 | C3u1 | D3u1 (S&R) | D3u2 | C3u2 | B3u2 | A3u2 (S&R) |
| A3d2 | B3d2 | C3d2 | D3d2 (S&R) | D3d1 | C3d1 | B3d1 | A3d1 |

A scan path of this type can be readily adapted for cases in which each well base is illuminated in multiple sections or parts other than quadrants. In all cases, the beam is shaped and positioned for illuminating a particular section of the base, and that section is illuminated and imaged for every well in a first row of wells in a plate. At the end of the row, the beam is reconfigured for a second section of the base and the well plate is shifted to align that section, before illumination and imaging of that section for every well in the first row, in a reverse direction to that used for the first section. This is repeated section by section throughout the first row of wells until every section has been illuminated and imaged, and then repeated for every row until the whole plate has been imaged.

It is to be emphasized that in the foregoing description, all references to imaging by illuminating a well base in four quadrants are merely for the sake of example. The various embodiments are all equally applicable to illumination of other fractions of the base, such as thirds, eighths, ninths, sixteenths, etc. The number of illuminations required per base will be determined by the size and shape of the beam (determined by the optical system employed) relative to the size of the wells. The various movements of the beam generating assembly and the well plate can be modified as necessary so that the base of every well is illuminated and imaged enough times to cover the whole of the base.

When imaging a whole well plate according to any of the above regimes, many short movements are required for multiple repositioning of the well plate and the imaging assembly. This can be complex to control with the accuracy required to properly align each quadrant of each well with the light beam and the camera, and also subjects the motors used to provide the movements to much wear. Additionally, if the well plate is moved, the many stops and starts and accompanying decelerations and accelerations may cause any liquid contents of the wells to move within the wells, which is liable to result in blurred images.

It is proposed to address these problems by providing constant speed continuous scanning movement. Assuming that the well plate is moved relative to the imaging assembly (although the opposite arrangement may be used), the well plate is moved according to a chosen scan path, such as that of FIG. 12. Using the example of FIG. 12, the movement brings each quadrant successively into line with the imaging assembly with a single continuous movement. As each quadrant comes into alignment, the camera shutter is opened and the illuminating light source is switched on, to record an image of that quadrant. The exposure time is arranged to be short enough compared to the speed of movement that the image is not blurred. This removes the need for accurate mechanical alignment for every image. Instead, the alignment is achieved in the time dimension by synchronizing the rate and duration of the exposures with the speed of movement of the well plate so that the images are taken at the appropriate time as each quadrant passes through the imaging assembly. To simplify this synchronization, the time for which the camera shutter is open may be arranged to be long compared to the time for which the light beam is switched on. The time that the beam is on thus defines the exposure time. Use of an appropriate light source, such as a flash lamp, that can provide very short pulses of light is a more straightforward way of providing the necessary brief exposure time than providing a camera with a very fast shutter response. The shorter the exposure time the faster the well plate can be moved without blurring of the images, thus giving more rapid imaging of a whole well plate.

Figure 13:
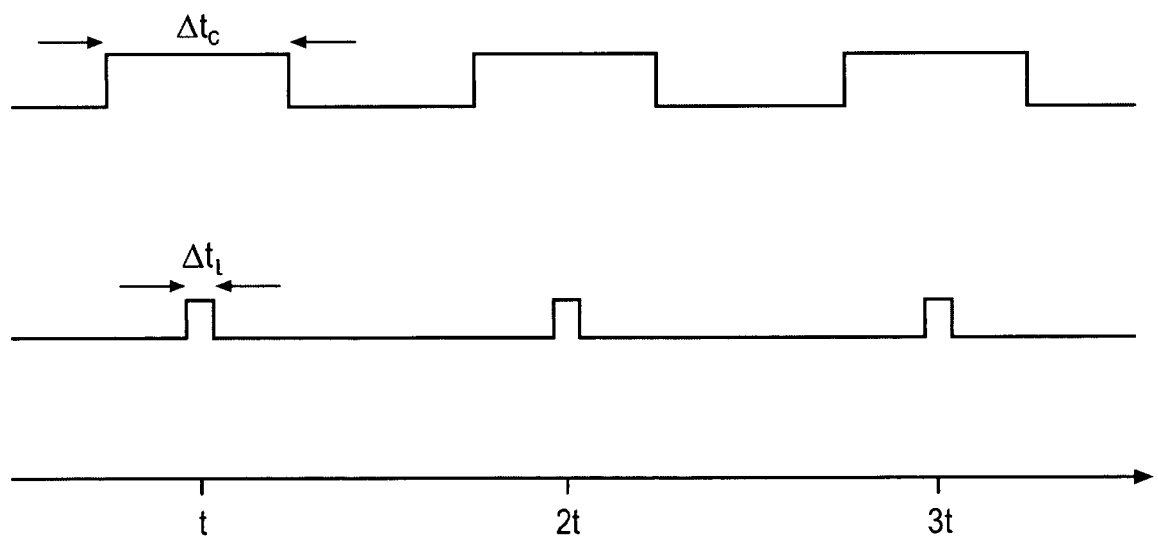
FIG. 13 shows graphs of the operation of a shutter in an imaging camera and of an optical beam source used for illuminating and imaging samples in a biological sample container according to an embodiment of the invention.

FIG. 13 shows schematic graphs representing the operation of the camera shutter and the light beam source in time, the upper graph representing the camera and the lower graph representing the light beam. Three imaging exposures are shown. Thus, for a constant speed of the well plate, the camera and light source are operated in synchronism at a constant repetition rate, spaced by time t. For a plate with wells spaced by distance d, moving at a speed v, the repetition rate is v/d. The camera shutter is opened for a duration $\Delta t_c$ and the light beam is switched on or pulsed for a duration $\Delta t_l$ within $\Delta t_c$, where $\Delta t_c > \Delta t_l$, and conveniently $\Delta t_c >> \Delta t_l$. For example, using a flash lamp that produces pulses of duration 3 μs, the camera may have a 10 ms exposure time. It may be necessary to reset the exposure at the end of the row of wells in the scan if the shift of the well plate and the rotation of the aperture, i.e. the mask in which the aperture is formed, cannot be accomplished in a time equal to the time between exposures (or a multiple thereof, in which case redundant images taken during this time can be discarded).

This imaging method is not limited to use with the described technique for imaging quadrants or other sections of wells in well plates. It can be readily applied to any sample imaging regime wherein separate images are to be taken of many regions in a single container. A single image of each well in a well plate might be taken, or a series of images across the extent of a single volume container such as a Petri dish. A scan path is defined which brings each region to be imaged in turn into the field of view of the imaging assembly, continuous relative movement is provided between the container and imaging assembly along this path, and the camera and light source operated in pulsed synchronism to coincide with alignment of each region with the imaging assembly.

An interesting variation is to scan the path two or more times at different focal planes of the imaging camera so that image "slices" are built up. Each time the path is traversed with a fixed focus of the imaging camera as described above so that multiple sets of images from the wells along each path are recorded corresponding to multiple well depths. The different focal planes may be defined by a single focusing activity. For example, the first scan could be at the depth determined by an autofocus on the base of the wells, and further scans could be performed at fixed offsets above the well base, such as in increments of a fixed percentage (e.g. 20%) of the total mechanically defined well depth, being the height from base to upper rim, or of the expected fill depth of a known volume of solution placed in each well (e.g. three slices at 0%, 50% and 100% of the expected fill depth of the wells).

For each embodiment of the imaging and scanning described above, the apparatus is preferably controlled by a controller such as a computer, to provide automated handling of biological sample containers.

Moreover, the imaging and scanning techniques may be usefully combined with the vacuum container holder. The ability of the holder to give an enhanced flatness to a container offers improved image quality over a series of images of different regions of the same container where there is no opportunity to refocus the imaging camera for every image, such as using continuous motion of the container, or when refocusing is undesirable.

The methods and apparatus described above may be advantageously combined with previously developed techniques described in co-pending U.S. patent application Ser. Nos. 10/631,845, 11/050,818 and 11/050,826 the contents of which patent applications are incorporated herein by reference.

Mechanical detachment methods may be used as described in the above patent applications. As an alternative to, or in combination with, mechanical detachment methods, adherent cells may be detached chemically, for example using buffers, salt solutions, detergents or biological materials, such as enzymes also as described in the above patent applications. Example media that can be placed in the wells to increase the efficiency by which cells can be dislodged are either an isotonic buffer containing different concentrations of divalent ions, or a buffer containing enzymes such as trypsin or proteases for releasing the cells from solid substrate. These media can be dispensed by a tube on the robotic head from the reservoir. After a period of incubation, normally between 5 and 20 minutes, a further medium may be added from another tube on the robotic head to stop the dissociation process. This isotonic medium may contain protein or divalent cations. The cell suspension can then be aspirated by a further tube on the robotic head and a measured aliquot of the cells dispensed into one or more wells in a destination well plate or multiple destination well plates. To assist incubation of an enzyme used to promote detachment, the well plate can beneficially be provided with a heated carrier element, such as a platen. For example, trypsin can be maintained at around 37 degrees Celsius to speed up its activity. In summary, animal cells may be replated out of the well plate using a medium to assist dislodging the animal cells. The medium may be a buffer containing divalent ions or enzymes. The medium may be maintained at an elevated temperature to promote its activity in dislodging the animal cells. Moreover, a mechanical shock may be applied to the well plate to assist dislodging of adherent animal cells.

In the above description, the optical source and detecting camera are mainly described as an illumination and imaging system without reference to spectroscopic properties. However, it will be understood that spectroscopic aspects can be incorporated into the apparatuses and methods of the invention. For example, the imaging may be of fluorescence or Raman properties.

The optical source may be configured to emit only at a particular fixed wavelength, or at a tunable or otherwise selectable wavelength. This may be done with the source itself, or through use of a broadband source in combination with appropriate filtering. The optical source system can be controllable to provide excitation at any one of a plurality of different wavelengths for selectively exciting a plurality of different dyes of interest. This may be done by providing a plurality of different types of optical source of different emission wavelengths, such as with different sources mounted at different "filter" positions on a filter wheel. Alternatively a tunable source may be used. The optical source system may also comprise a plurality of different bandpass filters for selecting light at different wavelengths for selectively exciting a plurality of different dyes of interest. This may be used in combination with a plurality of optical sources of different wavelength, with each filter being paired with a particular source. Alternatively, the filters may be used to filter a single broadband source to select a wavelength range targeted at a particular dye. The optical source system may comprise a white light source which may be used either as a fluorescence excitation source or for contrast imaging, or both.

The imaging camera may also be part of a collection optical system with spectroscopic capability. The collection optical system may comprise a plurality of different filters for assisting collection of light at different emission wavelengths associated with fluorescence from a plurality of different dyes of interest. The filters can conveniently be arranged on a filter wheel to allow automated selection via a central control system and to be placed in front of the sensitive part of the imaging camera. Typically this will be by acting to block light at the excitation wavelength used to excite fluorescence in the dye being used, and to transmit light at the emission wavelength of that dye.

Using the apparatus samples, typically cells, can be picked according to spectroscopic criteria. A cell may contain a compound that is present in greater or lesser amounts than the population as a whole. An example may be a cell or colony that has a high level of GFP (detected by fluorescence), a high level of metabolite (detected by Raman) or a pigment (detected by white light). These would all be endogenous. However, it is also possible to detect cells or clones that have altered spectral properties by adding exogenous reagents or compounds and measuring, using spectroscopic analysis, changes in spectral properties of a cell or colony or a component thereof. Examples would include adding a quenched dye to cells then stimulating the cells physiologically and using spectral changes (such as fluorescence) to measure calcium levels (Fura—2) or pH. The apparatus could then pick those colonies (based on the amount of emission or wavelength of the emission) that are high or low expressers.

Furthermore these spectral changes may be observed not only in the cells but also outside the cells as a consequence of components secreted into the medium from the cell. The components can be detected either directly, indirectly by the addition of a component such as a fluorescent antibody, or by an effect the component has upon the medium. There is also the case where the component straddles the membrane of the cell so is both inside and outside the cell.

There may be a single cell in the well, a number of individual cells, or cells formed in one or more colonies. The at least one cell may be an animal cell. The robot may be used for fluorescence studies, including bioluminescence, chemiluminescence and so forth, as well as for coloremetric studies, for example of red colonies. The cell or cells may express a biological molecule of interest. The biological molecule of interest can be selected from the group consisting of: a peptide, a polypeptide, a nucleic acid, a lipid, a metabolyte, or a glycosylated or unglycosylated protein. The biological molecule of interest may be a biopharmaceutical protein.

The cell or cells may themselves be marked with the dye, or contained in a medium which is marked with the dye whose optical activity is modified by secretion from the at least one cell. Example uses include assaying of individual cells or clones of cells for genetic changes by means of phenotypic markers that can be detected by changes within the cell or as a consequence of secretion from the cell or a combination of both. Examples include the identification of protease activities associated or missing from a cell by measuring the change in color or emission wavelength of an indicator in the medium. For example a quenched substrate within the medium may not exhibit fluorescence until it is cleaved by an enzyme or other activity. Measurements of changes in fluorescence with the robot are made to detect the activity. It will be understood that there are numerous assays applicable to these kinds of measurements, for example those exemplified in the Molecular Probes catalog.

The apparatus of the invention provides a versatile platform for this and a variety of other uses based around fluorescence measurements which may be spatially resolved within each measurement (fluorescence imaging) or may be limited to a single spectroscopic analysis for the data collected at each sample position, for example a single analysis for each well of a well plate.

The apparatus can be used to pick valuable or interesting cells or colonies of cells from a cell population. The cells may be 1 to 50 in number in the case of individual cells, or much greater in number in the case of colonies. Using the apparatus such cells can be picked according to spectroscopic criteria. A cell may contain a compound that is present in greater or lesser amounts than the population as a whole. An example may be a cell or colony that has a high level of GFP (detected by fluorescence), a high level of metabolite (detected by Raman) or a pigment (detected by white light). These would all be endogenous. However, it is also possible to detect cells or clones that have altered spectral properties by adding exogenous reagents or compounds and measuring, using spectroscopic analysis, changes in spectral properties of a cell or colony or a component thereof. Examples would include adding a quenched dye to cells then stimulating the cells physiologically and using spectral changes (such as fluorescence) to measure calcium levels (Fura—2) or pH. The apparatus could then pick those colonies (based on the amount of emission or wavelength of the emission) that are high or low expressers.

Furthermore these spectral changes may be observed not only in the cells but also outside the cells as a consequence of components secreted into the medium from the cell. The components can be detected either directly, indirectly by the addition of a component such as a fluorescent antibody, or by an effect the component has upon the medium. There is also the case where the component straddles the membrane of the cell so is both inside and outside the cell.

By way of example, the table below gives, for a number of useful dyes, suitable LED types for excitation LEDs of the optical beam source together with suitable pairs of excitation side filters and collection-side (i.e. emission) filters. The peak excitation and emission wavelengths $\lambda$ of the example dyes are also stated.

| Dye | Peak Excitation $\lambda$ (nm) | Peak Emission $\lambda$ (nm) | LED Type | Excitation Filter | Emission Filter (Chroma Co.) |
|---|---|---|---|---|---|
| BFP | 381 | 445 | UV | none | D460/50m |
| CFP | 434 | 477 | Royal Blue | D(HQ)450/50X | D505/40m |
| EGFP | 488 | 507 | Blue | D(HQ)470/40X | HQ535/50m |
| FITC | 490 | 525 | Blue | D(HQ)470/40X | HQ535/50m |
| YFP | 513 | 527 | Cyan | D(HQ)500/30X | D550/40m |
| Rhodamine | 550 | 573 | Green | D(HQ)530/30X | HQ590/50m |
| DSRed | 565 | 582 | Green | D(HQ)530/30X | HQ590/50m |
| Cy5 | 649 | 670 | Red | D(HQ)623/36X | HQ700/75m |

It will be appreciated that although particular embodiments of the invention have been described, many modifications/additions and/or substitutions may be made within the spirit and scope of the present invention.

REFERENCES

[1] U.S. Pat. No. 6,130,745 (Manian et al)
[2] U.S. Pat. No. 6,441,894 (Manian et al)
[3] EP 1,293,783 (Genetix Limited)

What is claimed is:

1. A method of imaging a biological sample in a well of a well plate, the well defined by a side wall and a base, the method comprising:
    illuminating the base of the well by directing downwardly onto the base of the well a beam of light so that part of the base is illuminated by light rays in the beam incident on the base that have not first passed through a part of the well plate, and repositioning at least one of the well and the beam to direct the beam onto a further part of the base as many times as necessary for every part of the base to be so illuminated;
    recording an image of the biological sample each time the base is illuminated, wherein the beam of light is directed onto the base so that no light ray in the beam incident on the base passes first through a part of the well plate, wherein the beam of light has a propagation axis and comprises light rays converging to a focus on the propagation axis, the beam being defined, in a plane parallel to the propagation axis, by a first light ray parallel to the propagation axis and a second light ray at an angle to the propagation axis, arranging in the beam a converging lens centered on the propagation axis and an aperture offset from the propagation axis that passes a fraction of the beam; and the directing comprises positioning the well in the beam before the focus so that the first light ray is substantially parallel to the side wall of the well.

2. The method of claim 1, wherein the beam of light is directed onto the base so that at least some light rays in the beam are incident on the base at an oblique angle, and wherein the or each image is recorded in a dark field configuration where light from the beam, if not scattered, does not contribute to the image.

3. The method of claim 1, wherein the converging lens and the aperture are positioned and the aperture is shaped and dimensioned to pass a fraction of the beam that illuminates approximately one quadrant of the base.

4. The method of claim 3, wherein the aperture is crescent-shaped with the propagation axis located within the curve of the crescent but outside the aperture.

5. The method of claim 1, wherein the beam is directed onto the base four times, each time illuminating a different quadrant of the base, and the repositioning the well and/or the beam comprises repositioning the beam by rotating the aperture about the propagation axis by 90, 180 or 270 degrees, and repositioning the well by linearly moving the well plate to bring the different quadrants into line with the repositioned beam.

6. The method of claim 1, further comprising repeating the illuminating and the recording for a plurality of wells in the well plate.

7. The method of claim 1, wherein illuminating every part of the base requires two or more parts of the base to be illuminated, and the method further comprises repeating the illuminating and the recording for many or all wells in the well plate.

8. The method of claim 7, comprising:
illuminating and recording an image for a first part of each well of the many or all wells;
illuminating and recording an image for a second part of each well of the many or all wells; and
if necessary repeating the illuminating and recording for further parts of each of the many or all wells until every part of each of the many or all wells has been illuminated.

9. The method of claim 7, wherein the well plate comprises an array of wells arranged in rows, and the method comprises:
illuminating and recording an image for a first part of each well in a first row;
illuminating and recording an image for a second part of each well in the first row;
if necessary repeating the illuminating and recording for further parts of each well in the first row until every part of each well in the first row has been illuminated;
illuminating and recording an image for a first part of each well in a second row;
illuminating and recording an image for a second part of each well in the second row;
if necessary repeating the illuminating and recording for further parts of each well in the second row until every part of each well in the second row has been illuminated; and
repeating the illuminating and recording for each further row in the well plate.

10. The method of claim 5, wherein the well plate comprises an array of wells arranged in rows, and the method comprises:
illuminating and recording an image for a first quadrant of each well in a first row in a consecutive sequence in a first direction along the row;
repositioning the well plate and/or the beam to illuminate a second quadrant of each well;
illuminating and recording an image for the second quadrant of each well in the first row in a consecutive sequence in a second direction along the row opposite to the first direction;
repositioning the well plate and/or the beam to illuminate a third quadrant of each well;
illuminating and recording an image for the third quadrant of each well in the first row in a consecutive sequence in the first direction along the row;
repositioning the well plate and/or the beam to illuminate a fourth quadrant of each well;
illuminating and recording an image for the fourth quadrant of each well in the first row in a consecutive sequence in the second direction; and
repeating the illuminating and recording for each further row in the well plate.

11. The method of claim 1, wherein the beam of light has a wavelength selected to excite a dye of interest with which the sample has been marked.

12. The method of claim 11, wherein the image is recorded by selectively collecting light of wavelengths associated with fluorescence, auto-fluorescence or Raman emission from the dye of interest.

13. The method of claim 12, wherein the sample is at least one cell.

14. The method of claim 13, wherein the dye is contained in the at least one cell.

15. The method of claim 14, wherein the at least one cell is contained in a medium which is marked with the dye whose optical activity is modified by secretion from the at least one cell.

16. The method of claim 15, wherein the secretion is a protein, nucleic acid, lipid, sugar, metabolite or drug.

17. The method of claim 13, wherein the dye is an inherent part of the at least one cell.

18. The method of claim 13, wherein the at least one cell is an animal cell.

19. The method of claim 18, wherein the at least one animal cell express a biological molecule of interest.

20. The method of claim 19, wherein the biological molecule of interest is selected from the group consisting of: a peptide, a polypeptide, a nucleic acid, a lipid, a metabolyte, a glycosylated or unglycosylated protein, and a biopharmaceutical protein.

21. The method of claim 11, wherein the dye is selected from the group consisting of: a protein, a nucleic acid, a lipid, a sugar, a metabolite, and a drug.

22. The method of claim 13, wherein the at least one cell is a protein, nucleic acid, lipid, sugar or metabolite.

23. The method of claim 13, wherein the at least one cell secretes an agent which is detected by white light, infra-red, or Raman spectroscopy.

24. The method of claim 13, wherein the at least one cell secretes an agent which is detected by addition to the at least one cell of a compound that is detected by autofluorescence.

25. The method of claim 13, wherein the at least one cell contains an agent detected by addition to the at least one cell of a compound that is detected by fluorescence, white light, infra-red, Raman spectroscopy, or autofluorescence.

26. The method of claim 13, wherein the at least one cell secretes an agent detected by addition to the at least one cell of a compound that is detected by fluorescence, white light, infra-red, Raman spectroscopy, or autofluorescence.

27. The method of claim 13, wherein the at least one cell has a membrane which contains an agent which is detected by addition to the at least one cell of a compound that is detected by fluorescence, white light, infra-red, Raman spectroscopy, or autofluorescence.

* * * * *